United States Patent
Sagi et al.

(10) Patent No.: US 12,291,578 B2
(45) Date of Patent: May 6, 2025

(54) ANTI-MATRIX METALLOPROTEINASE 7 (MMP-7) INHIBITORY ANTIBODY AND USES THEREOF

(71) Applicant: Yeda Research and Development Co. Ltd., Rehovot (IL)

(72) Inventors: Irit Sagi, Rehovot (IL); Vishnu Mohan, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 909 days.

(21) Appl. No.: 17/429,672

(22) PCT Filed: Feb. 10, 2020

(86) PCT No.: PCT/IL2020/050158
§ 371 (c)(1),
(2) Date: Aug. 10, 2021

(87) PCT Pub. No.: WO2020/161724
PCT Pub. Date: Aug. 13, 2020

(65) Prior Publication Data
US 2022/0106405 A1    Apr. 7, 2022

(30) Foreign Application Priority Data
Feb. 10, 2019  (IL) .......................... 264768

(51) Int. Cl.
| C07K 16/40 | (2006.01) |
| A61K 31/282 | (2006.01) |
| A61K 31/7068 | (2006.01) |
| A61K 39/00 | (2006.01) |
| A61P 35/00 | (2006.01) |
| C07K 16/30 | (2006.01) |

(52) U.S. Cl.
CPC ............ *C07K 16/40* (2013.01); *A61K 31/282* (2013.01); *A61K 31/7068* (2013.01); *A61K 39/00* (2013.01); *A61P 35/00* (2018.01); *C07K 16/303* (2013.01); *A61K 2039/505* (2013.01); *C07K 2317/34* (2013.01); *C07K 2317/55* (2013.01); *C07K 2317/565* (2013.01); *C07K 2317/73* (2013.01); *C07K 2317/76* (2013.01); *C07K 2317/92* (2013.01)

(58) Field of Classification Search
CPC .. C07K 16/40; C07K 16/303; C07K 2317/34; C07K 2317/55; C07K 2317/565; C07K 2317/73; C07K 2317/76; C07K 2317/92; A61K 31/282; A61K 31/7068; A61K 39/00; A61K 2039/505; A61K 39/3955; A61P 35/00; G01N 2333/96494; G01N 2800/52; G01N 33/57438; C12N 9/6491; C12Q 1/37; C12Y 304/24023

See application file for complete search history.

(56) References Cited

U.S. PATENT DOCUMENTS

2013/0209491 A1\* 8/2013 Sagi ...................... C07K 16/40
530/389.8
2014/0322236 A1  10/2014 Chambers et al.

FOREIGN PATENT DOCUMENTS

| CN | 102702348 | 10/2012 | |
| CN | 104271156 | 1/2015 | |
| CN | 107184974 | 9/2017 | |
| JP | 10-287700 | 10/1998 | |
| JP | 2010-519289 | 6/2010 | |
| WO | WO 2008/102359 | 8/2008 | |
| WO | WO-2008102359 A1 \* | 8/2008 | .......... A61K 31/675 |
| WO | WO 2012/056455 | 5/2012 | |
| WO | WO 2020/161724 | 8/2020 | |
| WO | WO 2020/161724 A9 | 11/2020 | |

OTHER PUBLICATIONS

Fukuda, Akihisa, et al. "Stat3 and MMP7 contribute to pancreatic ductal adenocarcinoma initiation and progression." Cancer cell 19.4 (2011): 441-455. (Year: 2011).\*
Dondelinger, Mathieu, et al. "Understanding the significance and implications of antibody numbering and antigen-binding surface/residue definition." Frontiers in immunology 9 (2018): 2278. (Year: 2018).\*
Dym, O. 6FBJ; "Monoclonal antibody targeting Matrix Metalloproteinase 7". Protein Data Bank. Jan. 30, 2019. https://doi.org/10.2210/pdb6fbj/pdb (Year: 2019).\*
Siena, Liboria, et al. "Gemcitabine sensitizes lung cancer cells to Fas/FasL systemâmediated killing." Immunology 141.2 (2014): 242-255. (Year: 2014).\*
Mitsiades, Nicholas, et al. "Matrix metalloproteinase-7-mediated cleavage of Fas ligand protects tumor cells from chemotherapeutic drug cytotoxicity." Cancer research 61.2 (2001): 577-581. (Year: 2001).\*
Mondal, Goutam, et al. "EGFR-targeted cationic polymeric mixed micelles for codelivery of gemcitabine and miR-205 for treating advanced pancreatic cancer." Molecular pharmaceutics 14.9 (2017): 3121-3133. (Year: 2017).\*
Levin, Maxim, et al. "Next generation matrix metalloproteinase inhibitorsâNovel strategies bring new prospects." Biochimica et Biophysica Acta (BBA)-Molecular Cell Research 1864.11 (2017): 1927-1939. (Year: 2017).\*

(Continued)

*Primary Examiner* — Julie Wu
*Assistant Examiner* — Bryan William Heck

(57) ABSTRACT

A method of treating a disease associated with imbalanced or abnormal activity of MMP-7 is diclosed. The method comprises administration of an antibody comprising an antigen recognition region which binds a catalytic site of MMP-7, having complementarity determining region amino acid sequences as set forth in: SEQ ID NOs: 3, 4 and 5 (CDR3), sequentially arranged from N to C on a light chain of the antibody; and SEQ ID NOs: 6, 7 and 8, sequentially arranged from N to C on a heavy chain of the antibody.

17 Claims, 15 Drawing Sheets

Specification includes a Sequence Listing.

(56) References Cited

OTHER PUBLICATIONS

Sakamoto, Hiroki, et al. "Comparison of standard-dose and low-dose gemcitabine regimens in pancreatic adenocarcinoma patients: a prospective randomized trial." Journal of gastroenterology 41 (2006): 70-76. (Year: 2006).*
Sela-Culang, Inbal, Vered Kunik, and Yanay Ofran. "The structural basis of antibody-antigen recognition." Frontiers in immunology 4 (2013): 302. (Year: 2013).*
Sela-Passwell, Netta, et al. "Antibodies targeting the catalytic zinc complex of activated matrix metalloproteinases show therapeutic potential." Nature medicine 18.1 (2012): 143-147. (Year: 2012).*
Winer, Arthur, Sylvia Adams, and Paolo Mignatti. "Matrix metalloproteinase inhibitors in cancer therapy: turning past failures into future successes." Molecular cancer therapeutics 17.6 (2018): 1147-1155. (Year: 2018).*
Almendro, Vanessa, et al. "The role of MMP7 and its cross-talk with the FAS/FASL system during the acquisition of chemoresistance to oxaliplatin." Plos one 4.3 (2009): e4728. (Year: 2009).*
Porter, Craig T., Gail J. Bartlett, and Janet M. Thornton. "The Catalytic Site Atlas: a resource of catalytic sites and residues identified in enzymes using structural data." Nucleic acids research 32.suppl_1 (2004): D129-D133. (Year: 2004).*
Notification of Office Action and Search Report Dated Jul. 22, 2023 From the National Intellectual Property Administration of the People's Republic of China Re. Application No. 202080027435.9. (11 Pages).
International Preliminary Report on Patentability Dated Aug. 19, 2021 From the International Bureau of WIPO Re. Application No. PCT/IL2020/050158. (9 Pages).
International Search Report and the Written Opinion Dated May 25, 2020 From the International Searching Authority Re. Application No. PCT/IL2020/050158. (20 Pages).
Office Action and Search Report Dated Nov. 18, 2019 From the Israel Patent Office Re. Application No. 264768. (10 Pages).
Cheng et al. "Triterpenes From Poria Cocos Suppress Growth and Invasiveness of Pancreatic Cancer Cells Through the Downregulation of MMP-7", International Journal of Oncology, XP055693638, 42(6): 1869-1874, Jun. 1, 2013.
Dym "6FBJ—Monoclonal Antibody Targeting Matrix Metalloproteinase 7", Protein Data Bank in Europe, XP055691785, 2 P., Jan. 30, 2019.
Huo et al. "MMP-7 (Matrilysin) Accelerated Growth of Human Umbilical Vein Endothelial Cells", Cancer Letters, XP055692693, 177(1): 95-100, Mar. 2002.
Ito et al. "The VEGF Angiogenic Switch of Fibroblasts Is Regulated by MMP-7 From Cancer Cells", Oncogene, XP055592688, 26(51): 7194-7203, Published Online May 21, 2007.
Kuhlmann et al. "Evaluation of Matrix Metalloproteinase 7 in Plasma and Pancreatic Juice as A Biomarker for Pancreatic Cancer", Cancer Epidemiology, Biomarkers and Prevention, XP055693440, 16(5): 886-891, May 1, 2007.
Mitsiades et al. "Matrix Metalloproteinase 7-Mediated Cleavage of Fas Ligand Protects Tumor Cells From Chemotheraputic Drug Cytotoxicity", Cancer Research, XP055694078, 61(2): 577-581, Jan. 15, 2001.
Mohan et al. "Novel Monoclonal Antibody Targeting Matrix Metalloproteinase 7 Shows Therapeutic Potential Against Pancreatic Cancer. Chain L, Light Chain", Database NCBI [Online], GencBank Accession No. 6FBJ_L, Database Accession No. 6FBJ_L, Feb. 1, 2019.
Sela-Passwell et al. "Antibodies Targeting the Catalytic Zinc Complex of Activated Matrix Metalloproteinases Show Therapeutic Potential", Nature Medicine, XP055019945, 18(1): 143-147, Published Online Dec. 25, 2011.
Tan et al. "Involvement of MMP-7 in Invasion of Pancreatic Cancer Cells Through Activation of the EGFR Mediated MEK-ERK Signal Transduction Pathway", Journal of Clinical Pathology, XP055692697, 58(12): 1242-1248, Dec. 2005.
English Translation Dated Jan. 23, 2024 of Notice of Reason(s) for Rejection Dated Jan. 4, 2024 From the Japan Patent Office Re. Application No. 2021-543346. (10 Pages).
Notice of Reason(s) for Rejection Dated Jan. 4, 2024 From the Japan Patent Office Re. Application No. 2021-543346. (9 pages).
Protein Data Bank Monoclonal Antibody Targeting Matrix Metalloproteinase 7, Protein Data Bank in Europe, Retrieved Online, pp. 1-10, Jan. 30, 2019.
Translation Dated Aug. 11, 2023 of Notification of Office Action Dated Jul. 22, 2023 From the State Intellectual Property Office of the People's Republic of China Re. Application No. 202080027435.9. (19 pages).
Onuma Kunishige Onuma, Pharmacia, 47(12): 1167-1168, 2011. (Japanese only).

* cited by examiner

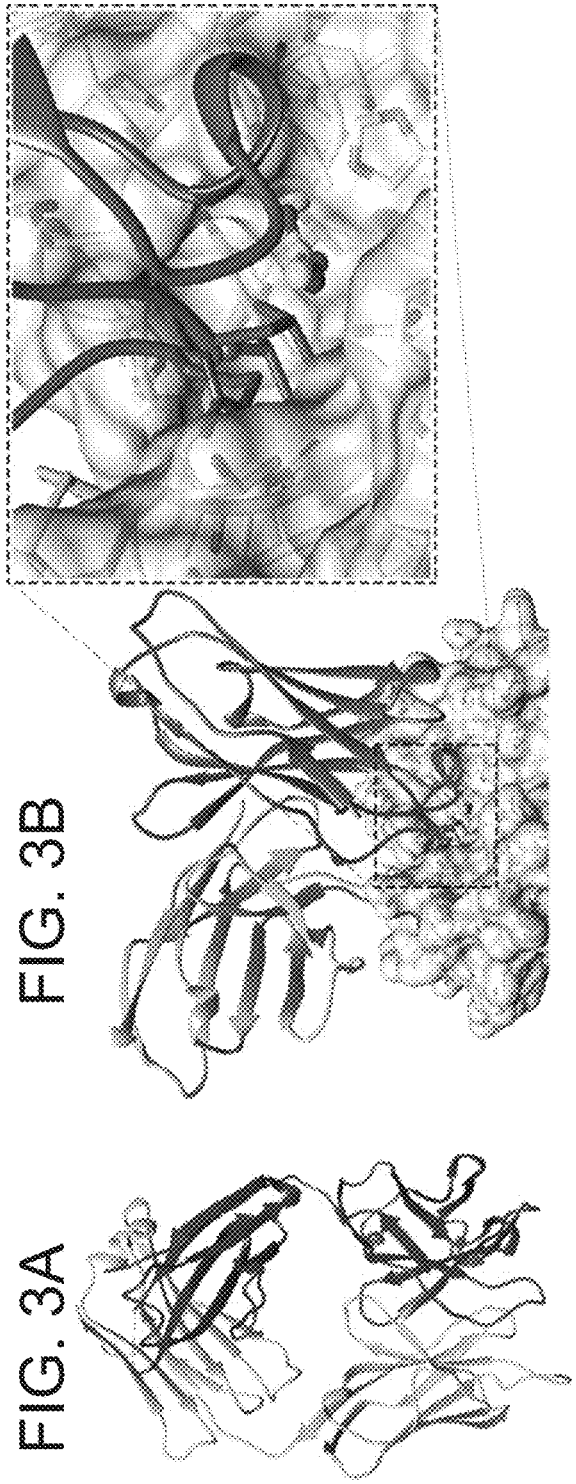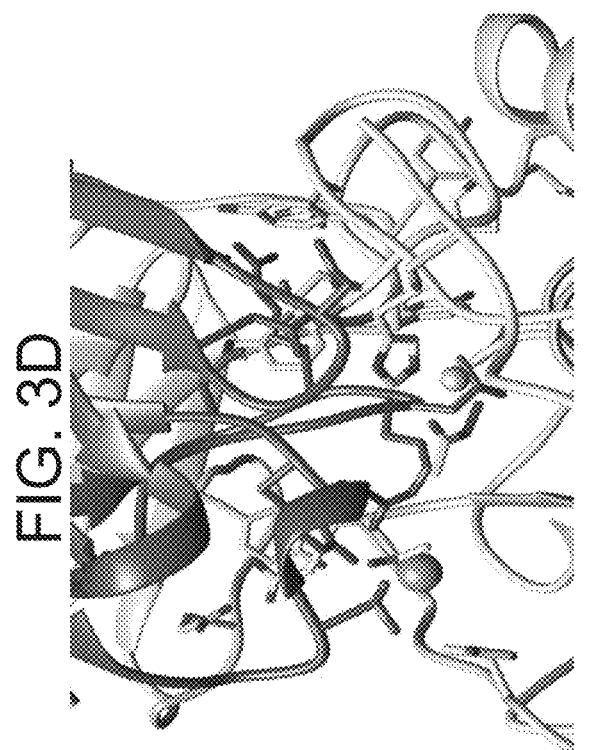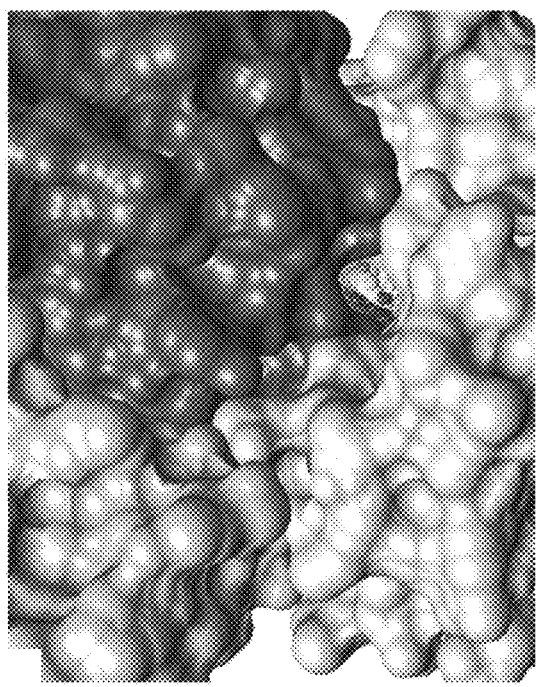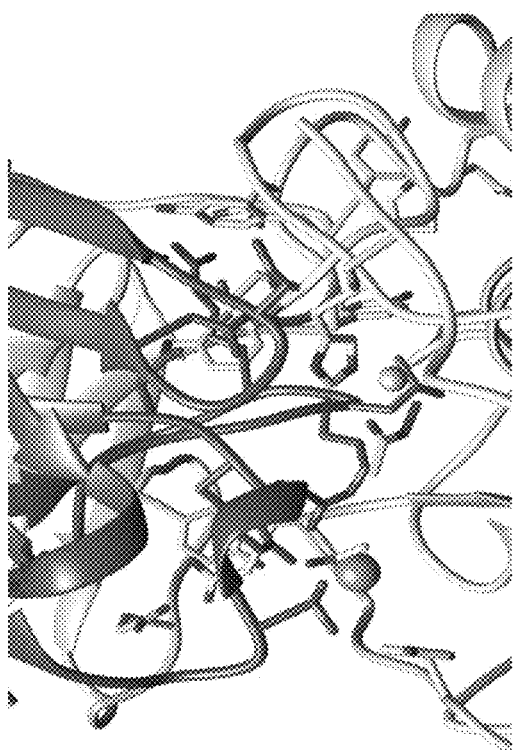

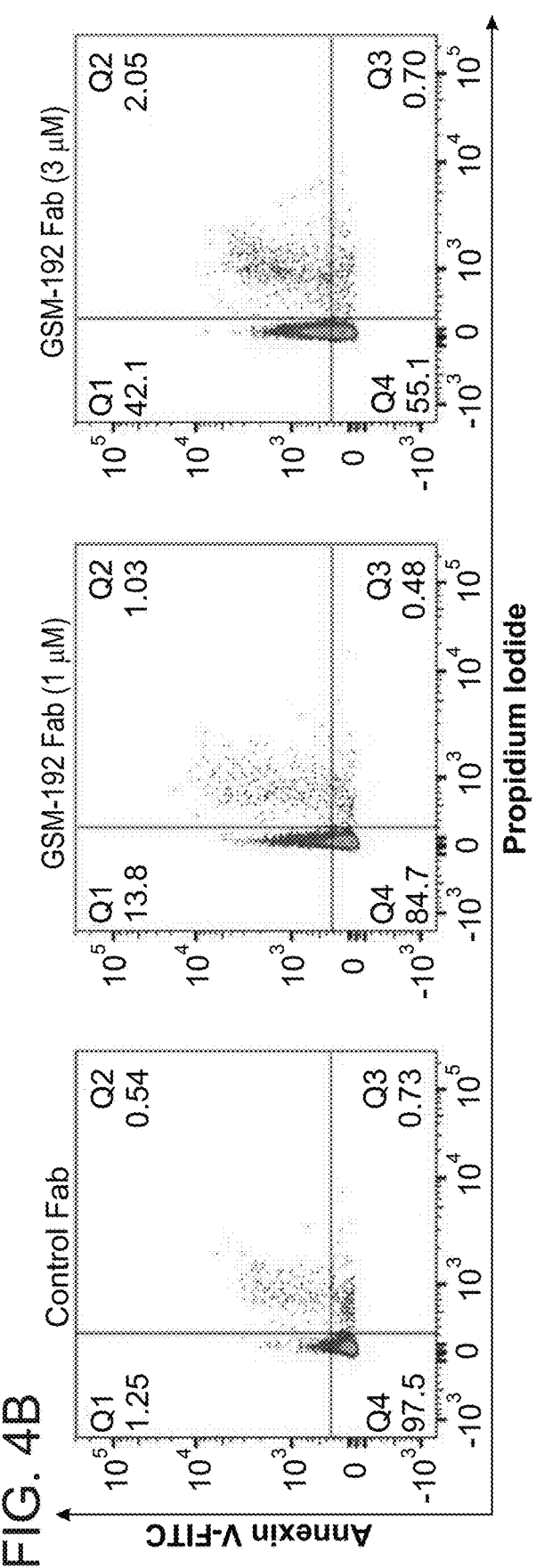
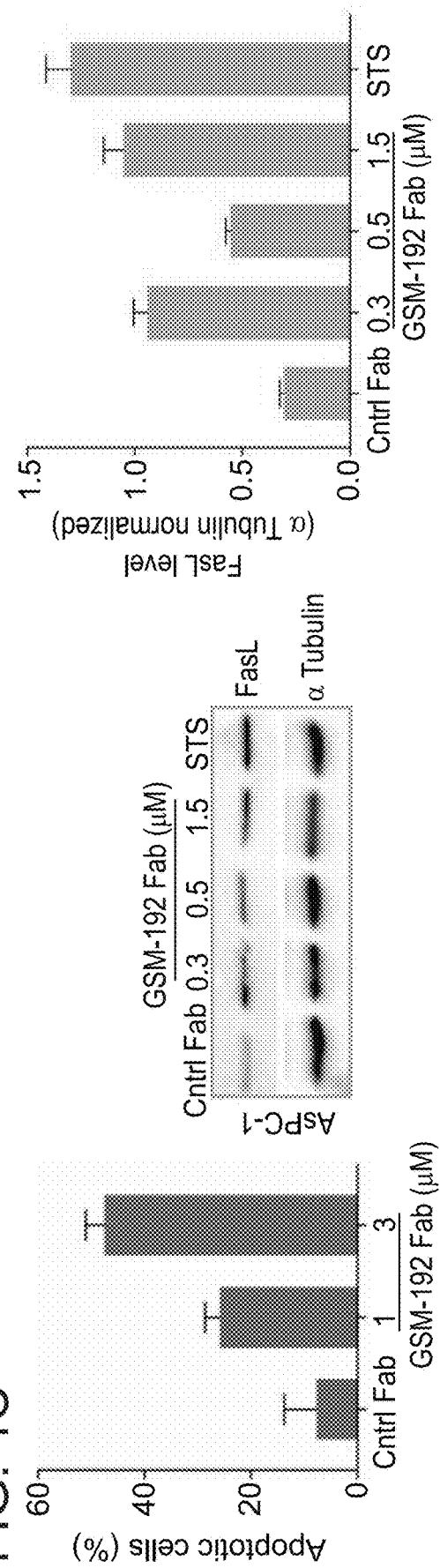
FIG. 4B
FIG. 4C

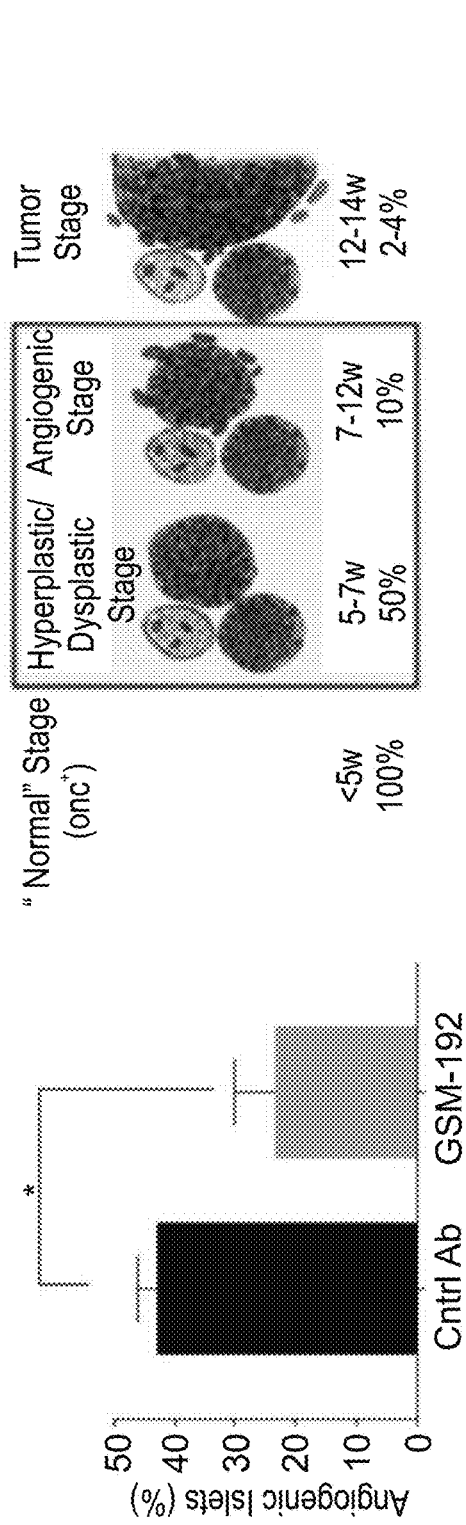
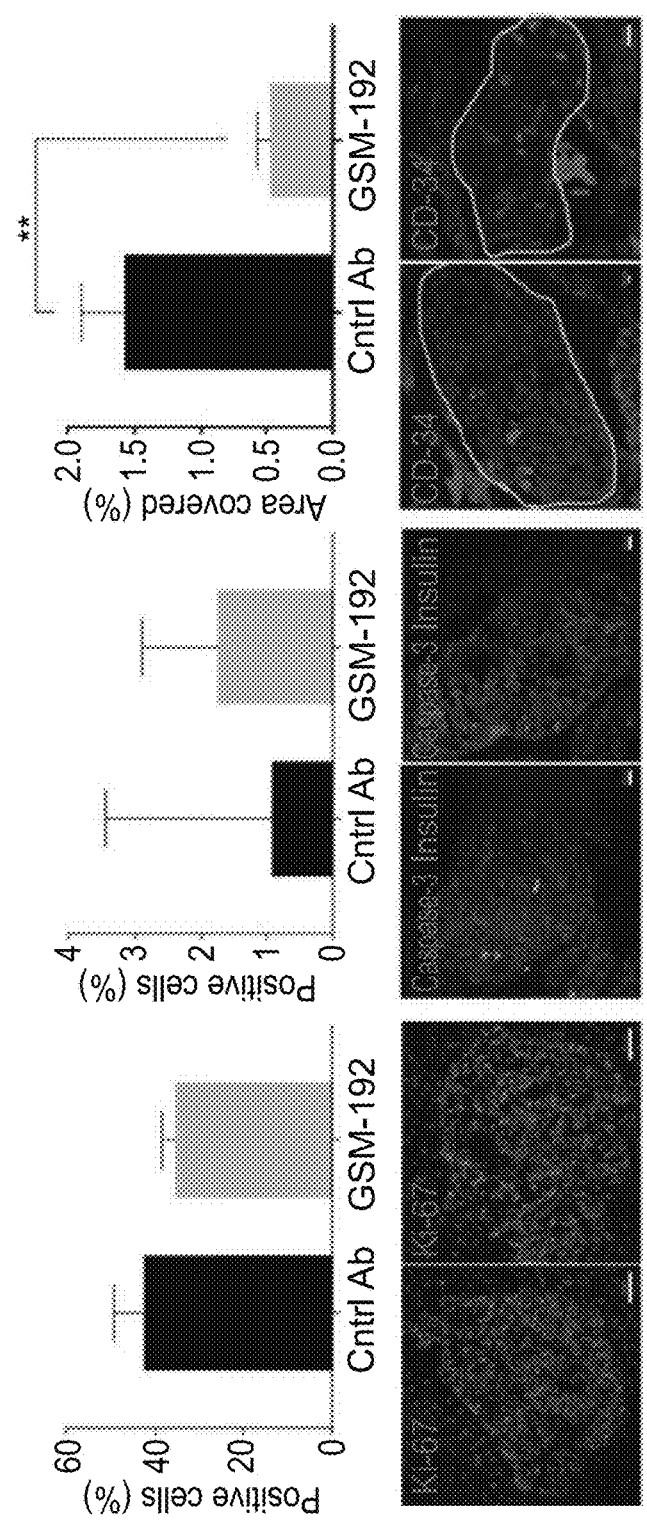
FIG. 9A
FIG. 9B

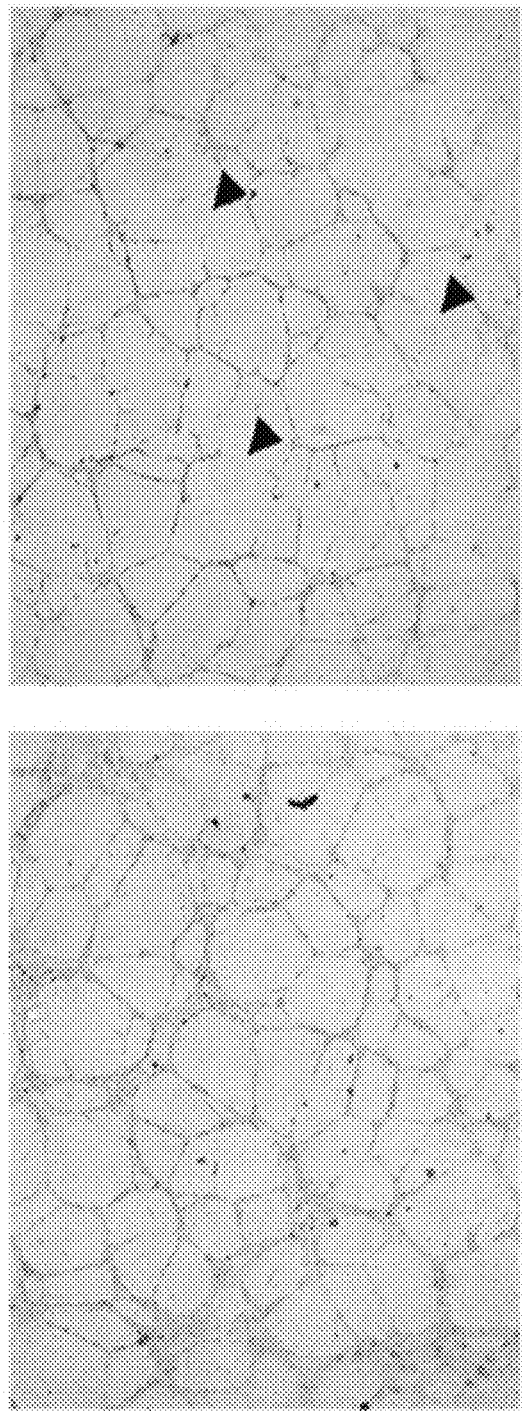
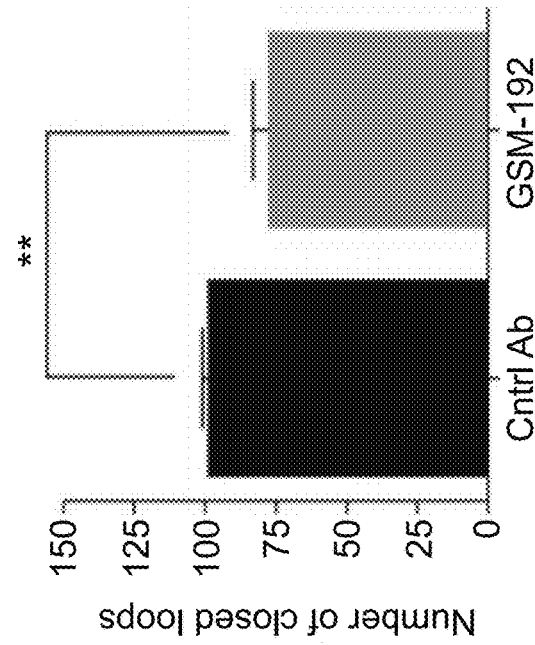
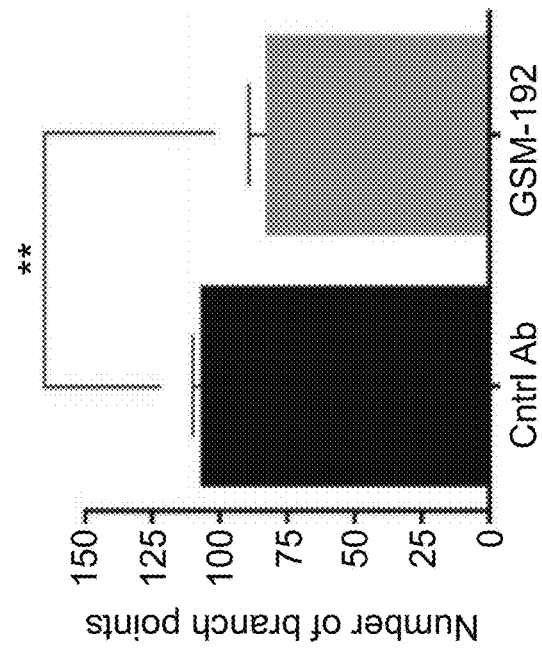
FIG. 10A

ANTI-MATRIX METALLOPROTEINASE 7 (MMP-7) INHIBITORY ANTIBODY AND USES THEREOF

RELATED APPLICATIONMAIS

This application is a National Phase of PCT Patent Application No. PCT/IL2020/050158 having International filing date of Feb. 10, 2020, which claims the benefit of priority of Israel Patent Application No. 264768 filed on Feb. 10, 2019. The contents of the above applications are all incorporated by reference as if fully set forth herein in their entirety.

SEQUENCE LISTING STATEMENT

The ASCII file, entitled 88766Sequence-Listing.txt, created on Aug. 10, 2021, comprising 4,599 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to an antibody that binds to the catalytic site of MMP-7. The antibody can be used for the treatment of cancer and, more particularly, but not exclusively, for the treatment of pancreatic cancer.

Matrix metalloproteinase 7 (MMP-7, matrilysin) has emerged as an important target for development of next generation cancer therapeutics due to its association with the clinical behaviour of multiple tumor types. It is an independent prognostic factor for overall survival in patients with advanced colorectal cancer. Ablation of MMP-7 significantly reduced tumor formation in multiple intestinal neoplasia mouse model. In similar fashion, an over expression of MMP-7 was found to accelerate tumor development in a MMTV-neu mouse breast cancer model. The mechanism by which MMP-7 contributes to early tumor growth is not yet well defined. MMP-7 null mouse have been shown to be prone to loss of metaplastic lesions following pancreatic ductal ligation and inhibition of MMP-7 with a broad spectrum MMP inhibitor reduced the number of intestinal polyps.

MMP-7 is unique among MMPs as it lacks a hemopexin-like domain and its main structure consists of a signal peptide, pro-peptide and zinc containing catalytic domain$_3$. MMP-7 is a secreted MMP, and like other MMPs is activated after cleavage of the pro-peptide. The proteases leading to its activation are yet to be fully defined. MMP-7 has been implicated in the breakdown of macromolecules like type IV collagen, gelatins, laminin, entactin/nidogen and tenascin-C. In addition to these classical enzymatic roles, MMP-7 has been implicated in modifying signaling pathways and regulating activity of cytokines. In the non-canonical signaling-related activity of MMP-7, the best-characterized substrates include Fas-L, Fas-R/CD-95, TNF-α, VEGF, Plasminogen, E-Cadherin, and integrin β-4. MMP-7 is involved in regulation of ErbB4 activity, induction of IL-17 mediated epithelial to mesenchymal transition and acts as pro-invasive effector molecule via the Wnt/β-catenin pathway. By these effects, MMP-7 acts on tumor cells as well as on stromal cells, rendering it an interesting target, with multiple downstream and upstream implications in both the protease web and signaling cascades. In pancreatic cancer, serum MMP-7 was recently shown to be a pre-operative prognostic marker, as its increased expression correlated with unresectable disease. Previous evidence indicated that MMP-7 in serum, plasma, and pancreatic juice is, along with related disease indicators, useful as a diagnostic marker.

Pancreatic cancer is a lethal, highly aggressive malignancy, estimated to become the second leading cause of cancer-related death in the United States by 2030. While its incidence is dramatically increasing, the treatment options for pancreatic cancer remain scarce and novel therapeutic strategies are urgently needed.

Background art includes WO2012/056455 which discloses antibodies generated against MMP-7.

SUMMARY OF THE INVENTION

According to an aspect of some embodiments of the present invention there is provided an antibody comprising an antigen recognition region which binds a catalytic site of MMP-7, having complementarity determining region (CDR) amino acid sequences as set forth in: SEQ ID NOs: 3 (CDR1), 4 (CDR2) and 5 (CDR3), sequentially arranged from N to C on a light chain of the antibody; and SEQ ID NOs: 6 (CDR1), 7 (CDR2) and 8 (CDR3), sequentially arranged from N to C on a heavy chain of the antibody.

According to an aspect of some embodiments of the present invention there is provided a method of treating a disease associated with imbalanced or abnormal activity of MMP-7 in a subject in need thereof, the method comprising administering to the subject a therapeutically effective amount of the antibody of claim 1, thereby treating the disease associate with imbalanced or abnormal activity of MMP-7 in the subject.

According to an aspect of some embodiments of the present invention there is provided a method of diagnosing a disease associated with imbalanced or abnormal activity of MMP-7 in a subject, the method comprising contacting a sample of the subject with the antibody described herein so as to analyze expression of MMP-7, wherein an upregulation of expression of the MMP-7 is indicative of the disease associated with imbalanced or abnormal activity of MMP-7.

According to an aspect of some embodiments of the present invention there is provided a method of treating cancer in a subject in need thereof comprising:

(a) analyzing in a sample of the subject for an amount of MMP-7; and (b) administering to the subject a therapeutically effective amount of the antibody described herein upon confirmation that the amount of the MMP-7 is above a predetermined level, thereby treating the cancer.

According to an aspect of some embodiments of the present invention there is provided a method of treating cancer in a subject in need thereof comprising:

(a) analyzing in a sample of the subject for an amount of MMP-7 using the antibody described herein; and (b) administering to the subject a therapeutically effective amount of an agent which down-regulates the amount of the MMP-7 upon confirmation that the amount of the MMP-7 is above a predetermined level, thereby treating the cancer.

According to an aspect of some embodiments of the present invention there is provided a method of treating pancreatic cancer in a subject in need thereof comprising administering to the subject a therapeutically effective amount of an antibody comprising an antigen recognition region which binds a catalytic site of MMP-7, wherein the antibody inhibits the activity of the MMP-7 and wherein the Ki of the antibody towards the MMP-7 is at least 5 times lower than a Ki of the antibody towards MMP2 or MMP9, thereby treating the pancreatic cancer.

According to an aspect of some embodiments of the present invention there is provided a pharmaceutical composition comprising the antibody described herein.

According to an aspect of some embodiments of the present invention there is provided an isolated polynucleotide encoding at least one CDR amino acid sequence selected from the group consisting of SEQ ID NOs: 3, 4, 5, 6, 7 and 8.

According to an aspect of some embodiments of the present invention there is provided an article of manufacture comprising the antibody described herein and a chemotherapeutic agent.

According to some embodiments of the invention, the antibody has a VL amino acid sequence as set forth in SEQ ID NO: 1.

According to some embodiments of the invention, the antibody has a VH amino acid sequence as set forth in SEQ ID NO: 2.

According to some embodiments of the invention, the antibody is attached to a detectable moiety or a therapeutic moiety.

According to some embodiments of the invention, the disease is cancer.

According to some embodiments of the invention, the cancer is pancreatic cancer.

According to some embodiments of the invention, the analyzing is effected using an antibody.

According to some embodiments of the invention, the antibody is the antibody described herein.

According to some embodiments of the invention, the polynucleotide encodes the CDR amino acid sequence as set forth in SEQ ID NOs: 3-5.

According to some embodiments of the invention, the polynucleotide encodes CDR amino acid sequence as set forth in SEQ ID NOs: 6-8.

According to some embodiments of the invention, the polynucleotide encodes the CDR amino acid sequence as set forth in SEQ ID NOs: 3-8.

According to some embodiments of the invention, the method further comprises administering to the subject a chemotherapeutic agent.

According to some embodiments of the invention, the chemotherapeutic agent is a nucleoside analogue.

According to some embodiments of the invention, the nucleotide analogue comprises gemcitabine.

According to some embodiments of the invention, the chemotherapeutic agent is Oxaliplatin.

According to some embodiments of the invention, the dose of the chemotherapeutic agent is less than the gold standard dose when used as a single agent.

According to some embodiments of the invention, the chemotherapeutic agent is a nucleoside analogue.

According to some embodiments of the invention, the nucleotide analogue comprises gemcitabine.

According to some embodiments of the invention, the chemotherapeutic agent is Oxaliplatin.

According to some embodiments of the invention, the antibody and the chemotherapeutic agent are formulated in a single composition.

According to some embodiments of the invention, the article of manufacture is for use in treating cancer.

According to some embodiments of the invention, the cancer is pancreatic cancer.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 3A-D. GSM-192 structure and docking showing antibody's unique affinity to binding sites close to the conserved active site within the activated form of the enzyme. A, Crystal structure (2.3 Å) of the Fab fragment of GSM-192 represented as a ribbon diagram. Heavy chain as well as light chain is shown (PDB: 6FBJ). B, The docking model of GSM-192 to activated human MMP-7 revealed direct binding to rim (exosites) of the enzyme active site. The surface of MMP-7 is shown and is made semi-transparent. The antibody is outlined showing three side chains: L100H, which is located near the Leu anchoring spot, R101H and Y33L. The latter interacts with MMP-7 at the active site anchoring exosites. Acetohydroxamic acid (AHA) is shown as balland-stick model with carbon atoms. C, Docking Structure of MMP-7 and GSM-192 complex showing excellent surface complementarity and a small "tunnel" through which the small inhibitor AHA can insert at the interface and bind to the Zn2+ ion. D, Ball and stick docking model showing important contacts near the active site Zinc.

FIGS. 4A-C. MMP-7 inhibition by both gene silencing and inhibitory antibody GSM-192 leads to tumor cell death in vitro. A, MMP-7 lentiviral silencing resulted in increased subG1 peak indicating a jump in AsPC-1 cell death, in a FACS based cell cycle analysis. Two vectors, lentivirus 1 (LV-1) and lentivirus 2 (LV-2) showed similar increase in sub G1 peak. B, MMP-7 inhibition leads to tumor cell death via apoptosis in AsPC-1 cells. FACS analysis showed increased Annexin V related apoptosis (Q1+Q2) after treatment with increasing dose of GSM-192 Fab. FACS data output here indicate early apoptotic cells as Q1, and late apoptotic cells as Q2. C, Increase in percentage of cells undergoing apoptosis was plotted using mean values ±s.e.m. (grey bar plot). LOXL-2 Fab generated using same pipeline was used as a treatment control.

Western Blot showing FasL expression in AspC-1 cell lysates with or without GSM-192 Fab treatment. An overall increase in FasL levels in anti MMP-7 Fab treated cells were observed. Anti LOXL-2 Fab at 1.5 µM concentration and staurosporine (STS), a pro apoptotic drug was used as treatment controls, α Tubulin was used as sample preparation control. Data in the graph represent α Tubulin normalized mean values ± s.e.m.

Figure 5A:
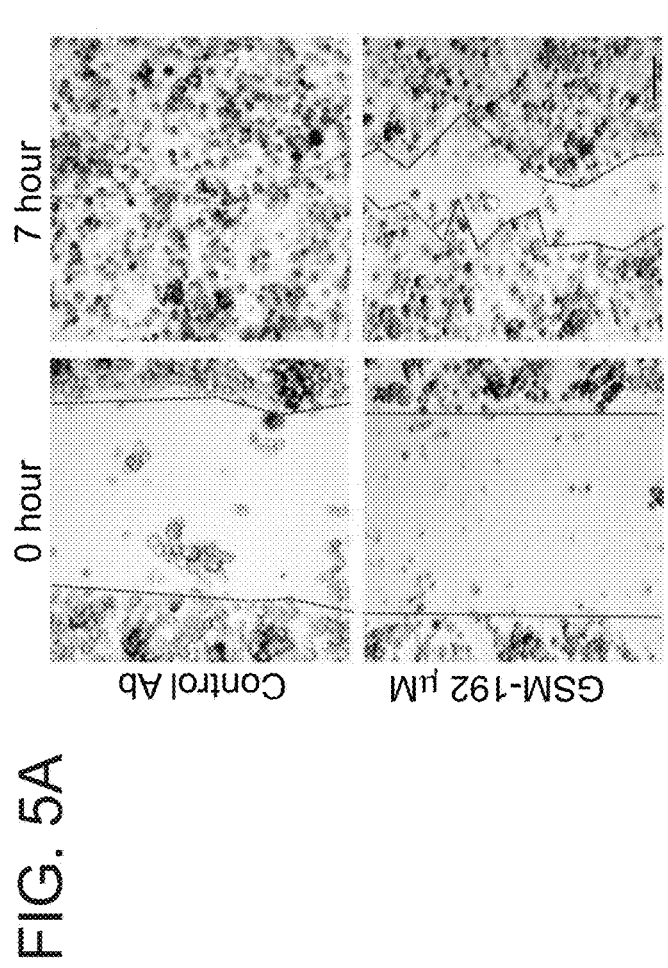
Figure 5B:
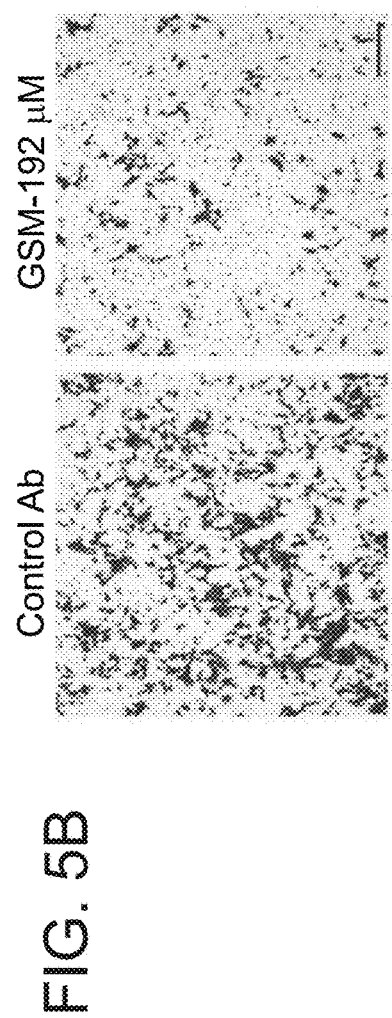

FIGS. 5A-B. GSM-192 treatment retards or reduces cell migration in scratch assay and transwell assay respectively. A, Treatment with GSM-192 slowed down cell migration in a standard scratch assay. 7 hours post treatment, control antibody GST (unspecific pooled IgG) treated wells close the scratch, but not the GSM-192 treated wells. Data represent mean values±s.e.m, and significance was evaluated with a two-tailed t-test. Scale bar, 20 µm. $P \leq 0.01$. B, GSM-192 reduces cells migrating across the transwell membrane significantly 15 hours post treatment. Data represent mean values±s.e.m., and significance was evaluated with a two-tailed t-test. Scale bar, 20 µm. *$P \leq 0.001$.

Figure 6B:
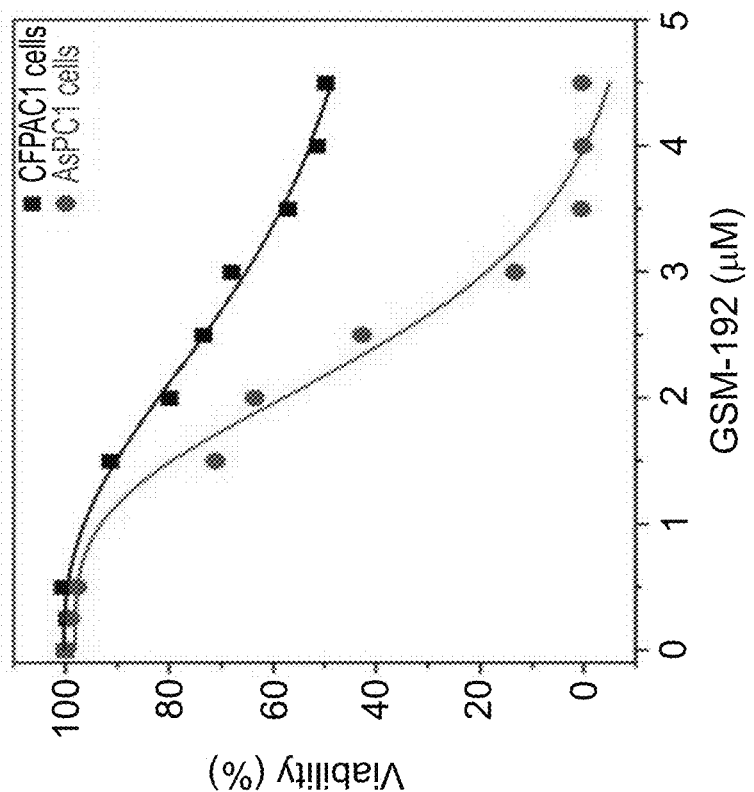
Figure 6A:
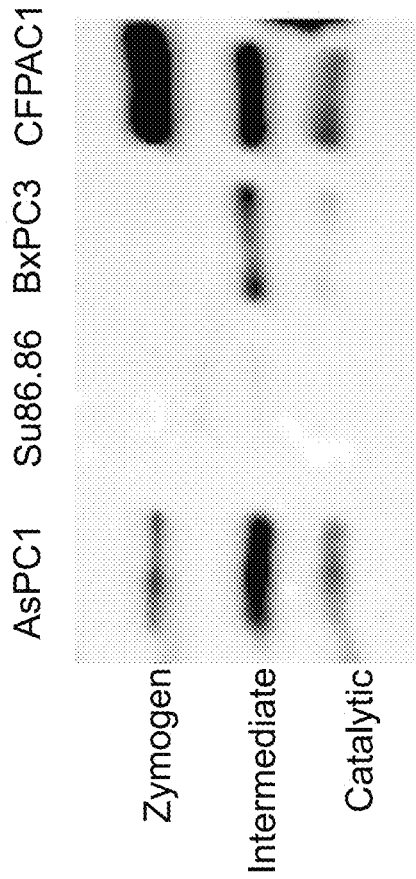

FIGS. 6A-B. MMP-7 expression and cell survival post GSM-192 treatment. A, Western blot analysis of cell culture media showing MMP-7 expression in various pancreatic cancer cell lines. B, The MTT cell survival assay was used to generate dose response curve-fitting analysis and IC 50 values for varying concentrations of GSM-192 treatment on AsPC-1 and CFPAC-1 pancreatic ductal adenocarcinoma cells were obtained. These $IC_{50}$ concentrations 2.33 µM for AsPC-1 and 4.34 µM for CFPAC-1 informed choice of Ab concentration for further experiments.

Figures 7A, 7B:
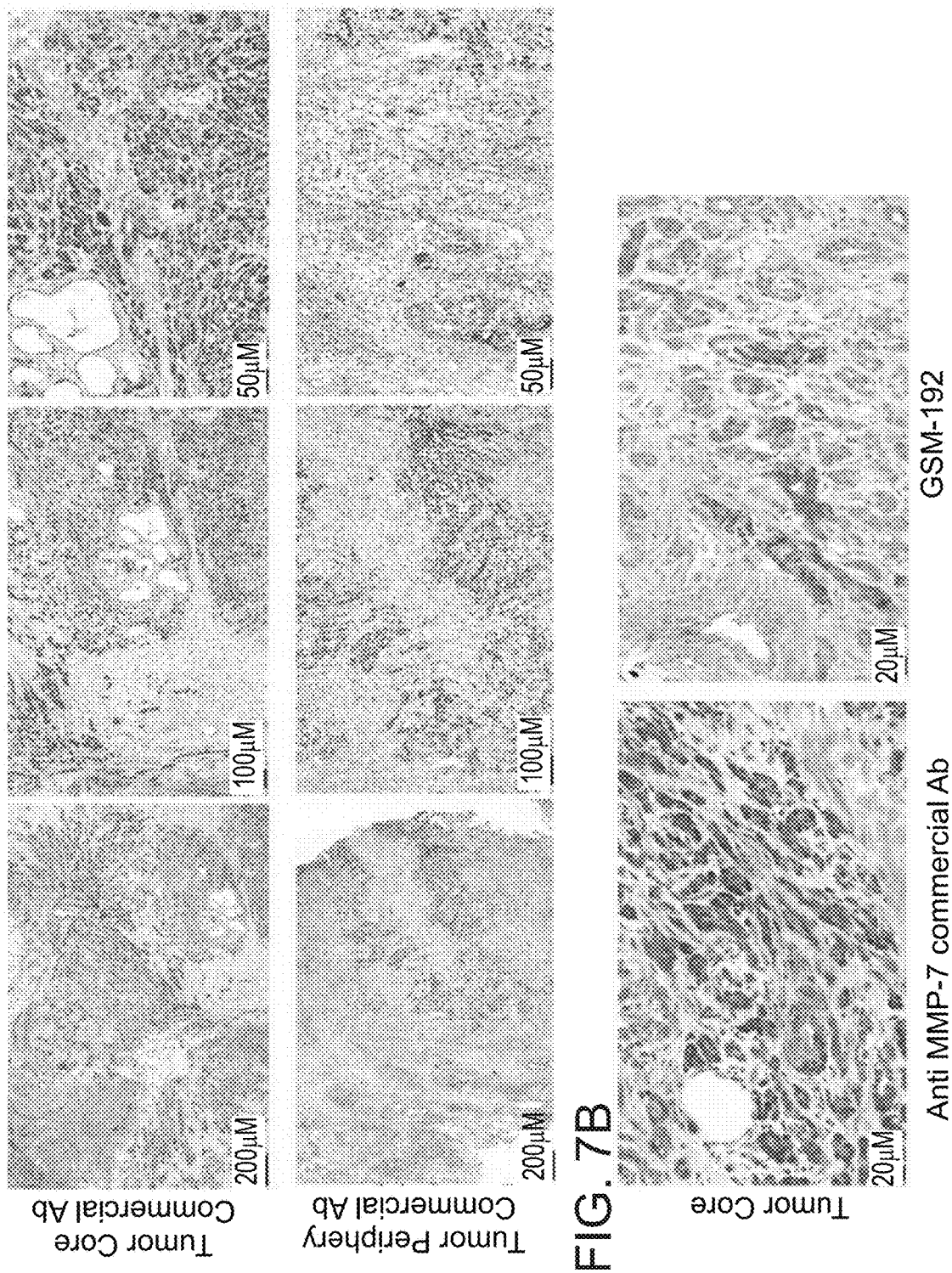

FIGS. 7A-B. Immunohistochemistry staining of human PDAC tissue with GSM-192. A, commercial anti MMP-7 Ab staining shows increased expression on MMP-7 protein in core compared to periphery of human PDAC tumor. B, A comparison of the GSM-192 and anti MMP-7 commercial antibody staining shows differential localization. GSM-192 predominantly stained active enzyme on cell surface and commercial antibody stained both zymogen and catalytic enzyme in nuclear and cytoplasmic compartment. Scale=20 µm.

Figure 8:
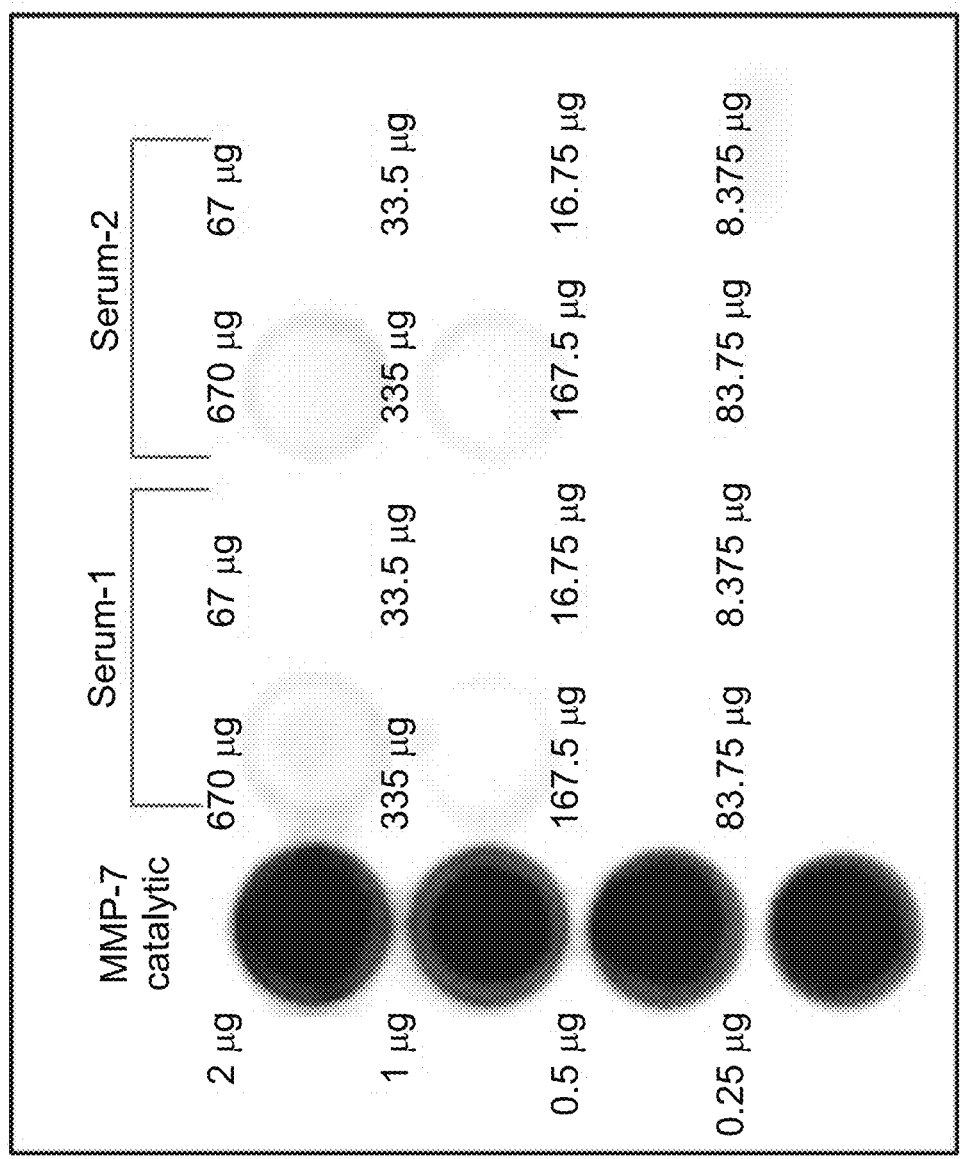

FIG. 8. Anti MMP-7mAb does not get sequestered by circulating MMP in RIP1-Tag2 mice serum. Compared to pure catalytic MMP-7, the antibody does not bind to a large range of total serum proteins derived from mice with advanced insulinoma (13.5 weeks). It is indicative of the lack of MMP-7 in catalytic form in blood and the high specificity of the anti MMP-7 antibody to the catalytic enzyme. The antibody thus is not susceptible to removing circulating enzyme or being removed as a result of binding.

Figure 9C:
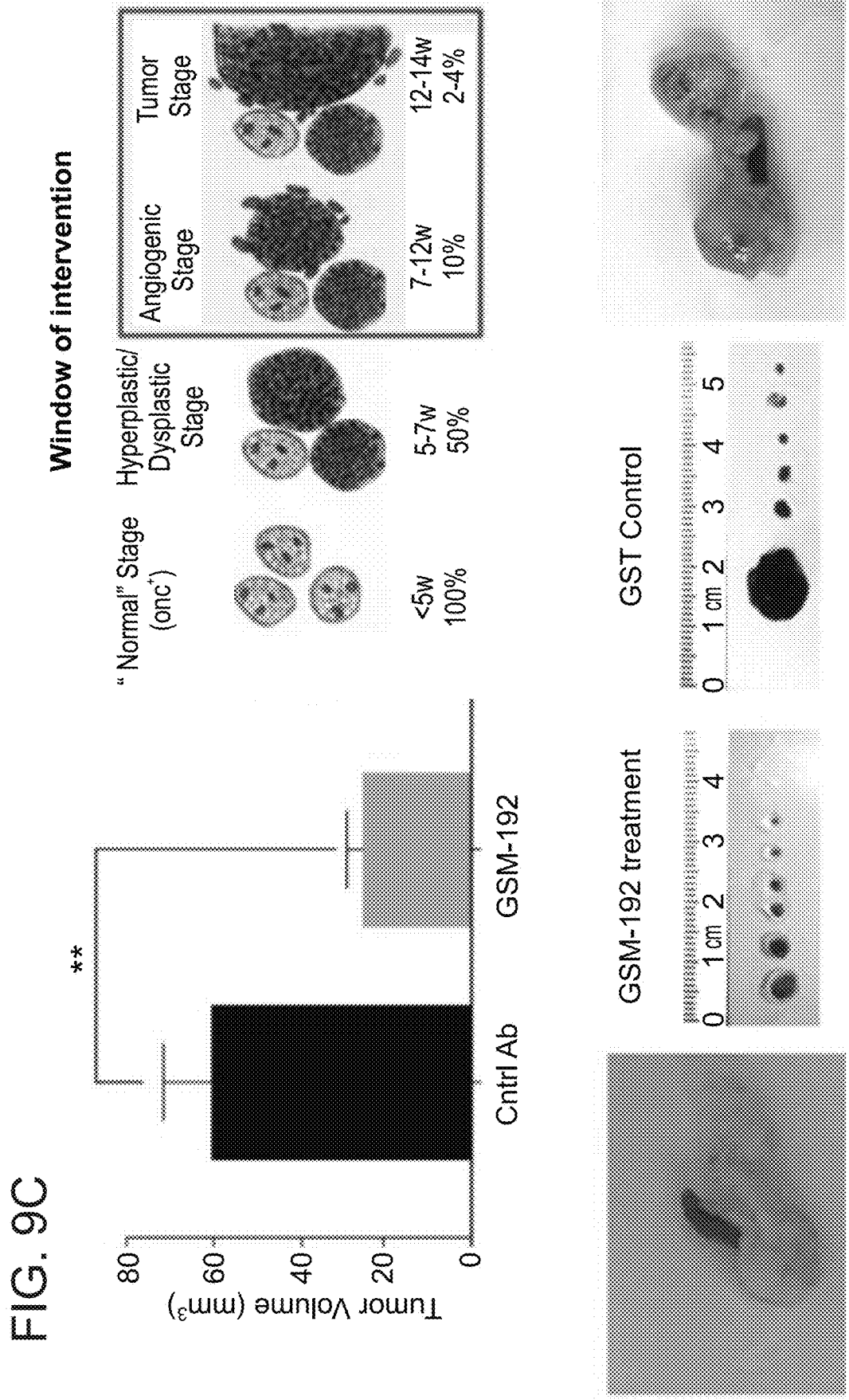

FIGS. 9A-C. A, Early stage treatment overall reduces number of islets undergoing angiogenic switch in RIP1-Tag2 insulinoma (PanNET) model. The number of angiogenic islets in GSM-192 treated mice were half of the total seen in control mice. B, In-vivo, the anti MMP-7 mAb does not show significant difference in numbers of Ki-67 and Capspase-3 positive cells, but it reduces the area covered by CD34+ cells in islets undergoing angiogenesis. C, Late stage treatment shows sustained effect on tumor volume in RIP1-Tag2 mouse model. The total tumor volume is aggregate volume of all tumor loci as shown. It is significantly reduced in treated vs. control mice. **$P \leq 0.01$, *$P \leq 0.05$.

Figure 10B:
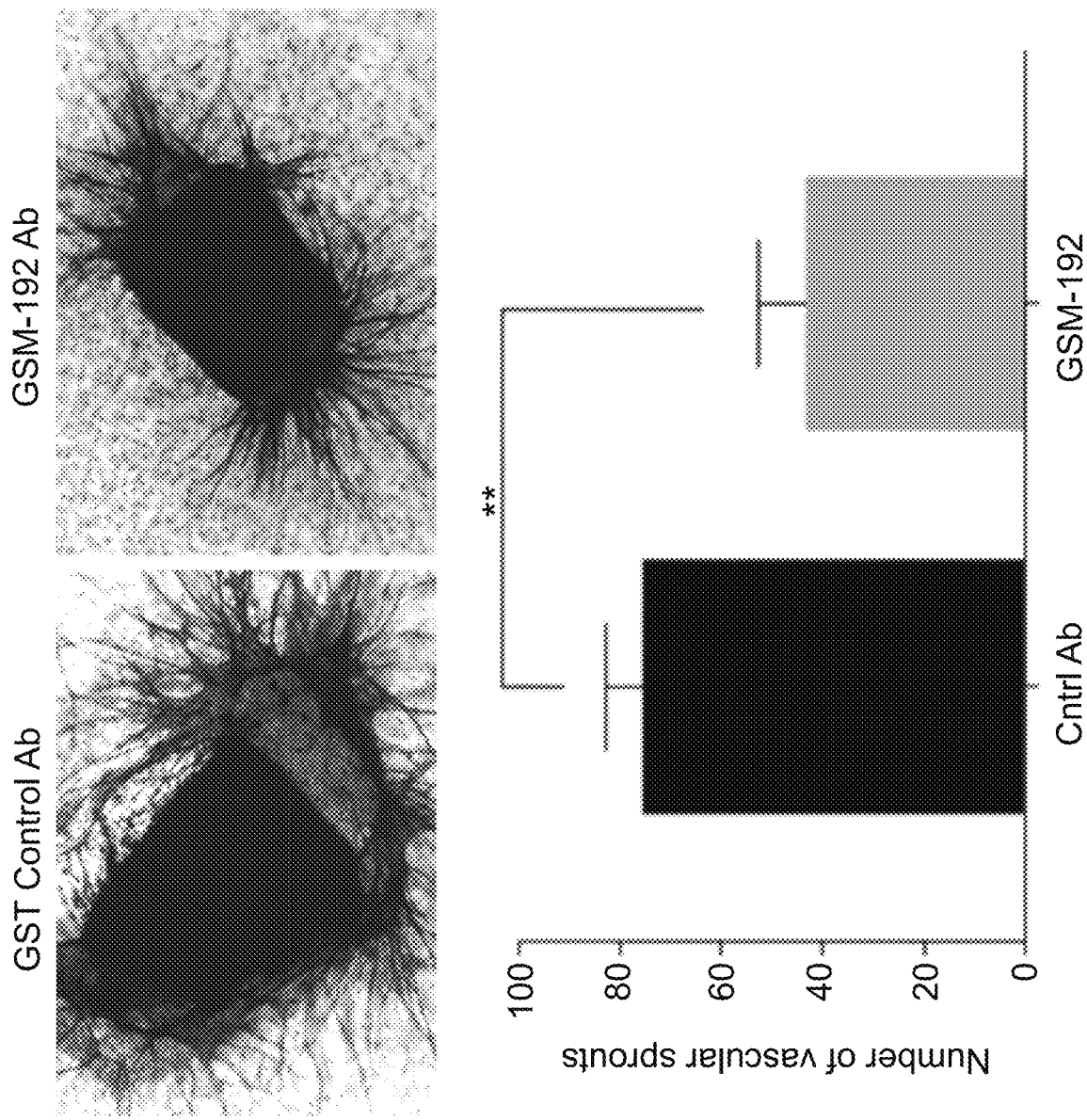

FIGS. 10A-B. A, Tube formation by HUVEC cells were disrupted when treated with 1 µM GSM-192. The total number of closed loops and branch points were significantly reduced in treated groups compared to GST control antibody treated group. B, Aortic ring sprout assay showed marked reduction of neo vascular sprouts with 1 µM GSM-192. The sprouts reduced significantly in GSM-192 treated group 7 days post ex-vivo incubation. These results demonstrate direct impact on angiogenesis post treatment with GSM-192.

Figure 11A:
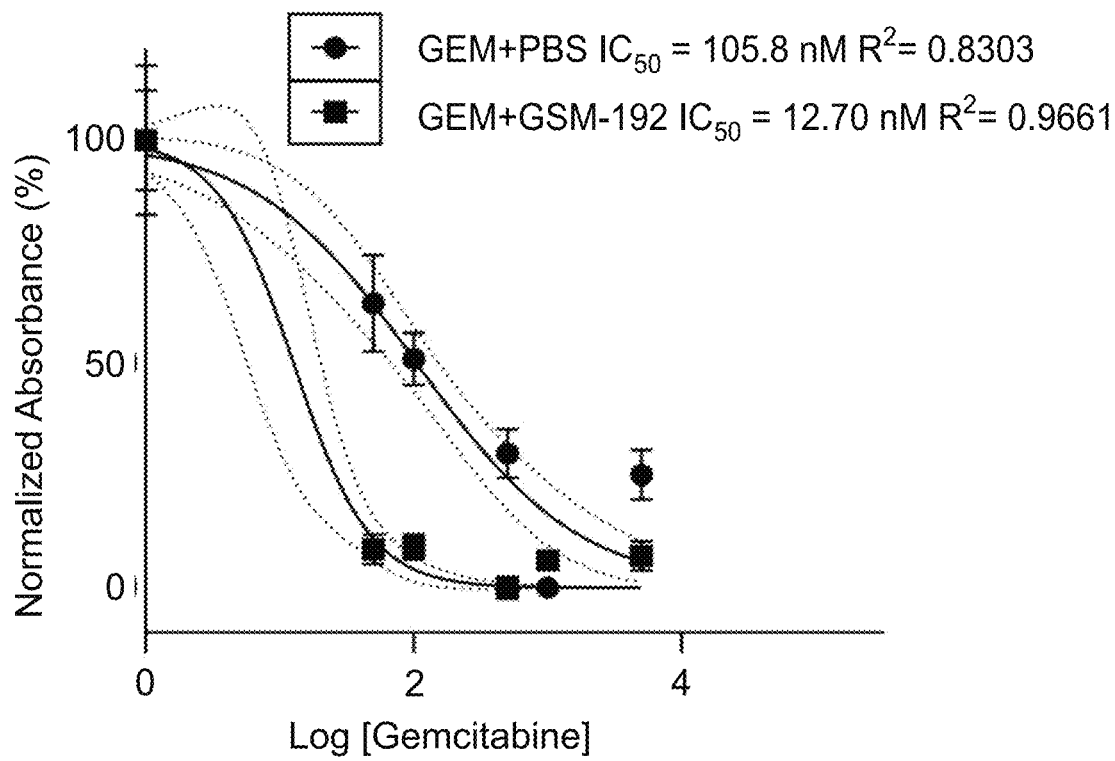
Figure 11B:
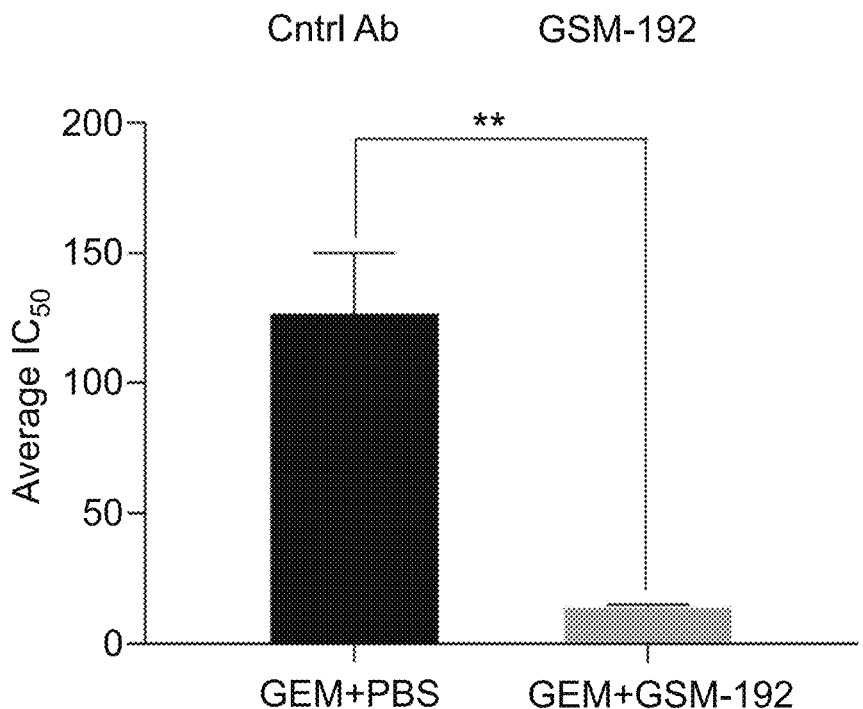

FIGS. 11A-B. A, MTT cell death assay absorbance data plotted as a function of the log of Gemcitabine (GEM) concentration and fitted on a variable slope sigmoidal regression model show markedly reduced $IC_{50}$ of GEM+ GSM-192 group compared to the GEM+PBS group. B, An average $IC_{50}$ of 3 such independent experimental curve fitting analysis was subsequently plotted to show significant difference between the groups. Data represent mean values±s.e.m., and significance was evaluated with a two-tailed t-test.

DESCRIPTION OF SPECIFIC EMBODIMENTS
OF THE INVENTION

The present invention, in some embodiments thereof, relates to an antibody that binds to the catalytic site of MMP-7. The antibody can be used for the treatment of cancer and, more particularly, but not exclusively, for the treatment of pancreatic cancer.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Matrix metalloproteases participate in many biological processes, ranging from cell proliferation, differentiation and remodeling of the extracellular matrix (ECM) to vascularization and cell migration. These processes require a delicate balance between the functions of the matrix metalloproteases (MMPs) and natural tissue inhibitors thereof (TIMPs). The loss of this balance is the hallmark of numerous pathological conditions including metastatic tumors, neurodegenerative diseases and osteoarthritis.

Numerous MMP inhibitors are known in the art including small peptide inhibitors such as hydroxamate, non-microbial tetracyclins and monoclonal antibodies.

The present inventors previously uncovered that antibodies which recognize both electronic and structural determinants of the catalytic site of metalloenzymes can be used as potent inhibitors thereof. Using haptens which mimic the metal-bound catalytic site of metalloenzymes as immunogens enabled the generation of highly efficient therapeutic antibodies which were shown to be able to treat clinical conditions characterized by elevated metalloprotein activity (see WO2004/087042 and WO2008/102359).

The present inventors have now understood that an additional screening step is imperative to uncover highly specific MMP-7 antibodies. Only antibodies that are capable of binding to the activated form of MMP-7 and not the zymogen should be selected for further development (i.e. selected for fusion and developed to generate monoclonal antibodies). The present inventors performed this step by carrying out dot blot analyses, using a nitrocellulose membrane coated with varying concentrations of active MMP-7 and its zymogen respectively. By carrying out this additional assay, the present inventors uncovered a highly specific monoclonal antibody to MMP-7, referred to herein as GSM-192 that binds to the catalytic domain of the enzyme and not the zymogen form of the enzyme.

Docking of the Fv domains of GSM-192 to available MMP-7 structures suggested GSM-192 to be effective in binding the catalytic cleft region (FIGS. 3A-D), producing a stearic hindrance blocking entry of substrate molecules.

Figure 4A:
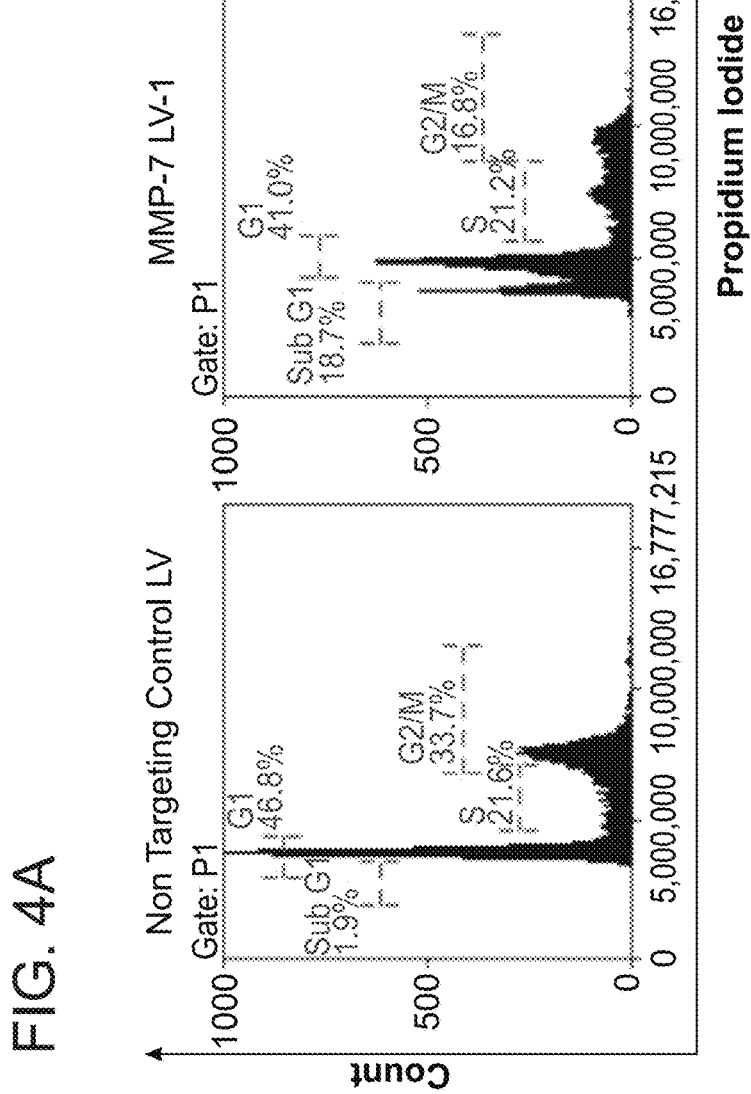

Whilst analysing the specificity of this antibody, the present inventors found that GSM-192 bound MMP-7 with impressive selectivity and affinity when compared to related MMPs (FIGS. 2A-F). Inhibition of MMP-7 using GSM-192 Fab induced cell death in pancreatic cancer cells in a concentration-dependent manner. Treatment of PDAC human cells with GSM-192 led to a concentration dependent stabilization of the major extrinsic death pathway ligand—Fas ligand. Thus, inhibition of active MMP-7 led to cell death in vitro with a concomitant increase in cell surface Fas ligand in the treated group (FIGS. 4A-C). Without being bound to theory, it may be concluded that inhibition of MMP-7 by GSM-192 may be due to the blockage of one of the downstream functions of MMP-7, namely protecting cancer cells from FasL-induced apoptosis. Furthermore, GSM-192 treatment of PDAC cells (CFPAC-1) impaired their ability to migrate through transwell pores and close an artificial wound in a scratch assay (FIGS. 5A-B). In conclusion, specific inhibition of MMP-7 using a high affinity novel antibody further corroborated its role as a crucial target in pancreatic cancer progression.

The present inventors propose that antibodies such as GSM-192 may have a significant and direct impact on therapeutic, diagnostic and research applications. Specifically, for diagnostic applications, antibodies, which recognize the active conformation of MMPs, are valuable, because diseased tissues show marked differential expression of the activated forms over their zymogen.

Thus, according to a first aspect of the present invention, there is provided an antibody comprising an antigen recognition region which binds a catalytic site of MMP-7, having complementarity determining region (CDR) amino acid sequences as set forth in: SEQ ID NOs: 3 (CDR1), 4 (CDR2) and 5 (CDR3), sequentially arranged from N to C on a light chain of the antibody; and SEQ ID NOs: 7 (CDR1), 8 (CDR2) and 9 (CDR3), sequentially arranged from N to C on a heavy chain of the antibody.

The antibody of this aspect of the present invention may comprise a VH amino acid sequence as set forth in SEQ ID NO: 2 and a VL amino acid sequence as set forth in SEQ ID NO: 1. The CDR sequences of the antibody are provided in SEQ ID NOs. 3-8.

According to a particular embodiment, the antibody comprises the amino acid sequences at least 90% homologous, at least 91% homologous, at least 92% homologous, least 93% homologous, at least 94% homologous, at least 95% homologous, least 96% homologous, at least 97% homologous, at least 98% homologous, at least 99% homologous or even 100% homologous to the sequences as set forth in SEQ ID NO: 1 and 2 (wherein the CDR sequences of the antibody are always 100% homologous to those provided herein above).

As used herein the term "antibody", refers to an intact antibody molecule and the phrase "antibody fragment" refers to a functional fragment thereof, such as Fab, F(ab')2, and Fv that are capable of binding to macrophages. These functional antibody fragments are defined as follows: (i) Fab, the fragment which contains a monovalent antigen-binding fragment of an antibody molecule, can be produced by digestion of whole antibody with the enzyme papain to yield an intact light chain and a portion of one heavy chain; (ii) Fab', the fragment of an antibody molecule that can be obtained by treating whole antibody with pepsin, followed by reduction, to yield an intact light chain and a portion of the heavy chain; two Fab' fragments are obtained per antibody molecule; (iii) (Fab')$_2$, the fragment of the antibody that can be obtained by treating whole antibody with the enzyme pepsin without subsequent reduction; F(ab')2 is a dimer of two Fab' fragments held together by two disulfide bonds; (iv) Fv, defined as a genetically engineered fragment containing the variable region of the light chain and the variable region of the heavy chain expressed as two chains; (v) Single chain antibody ("SCA"), a genetically engineered molecule containing the variable region of the light chain and the variable region of the heavy chain, linked by a suitable polypeptide linker as a genetically fused single chain molecule; and (vi) Peptides coding for a single complementarity-determining region (CDR).

As used herein, the terms "complementarity-determining region" or "CDR" are used interchangeably to refer to the antigen binding regions found within the variable region of the heavy and light chain polypeptides. Generally, antibodies comprise three CDRs in each of the VH (CDR HI or HI; CDR H2 or H2; and CDR H3 or H3) and three in each of the VL (CDR LI or LI; CDR L2 or L2; and CDR L3 or L3).

The identity of the amino acid residues in a particular antibody that make up a variable region or a CDR can be determined using methods well known in the art and include methods such as sequence variability as defined by Kabat et al. (See, e.g., Kabat et al., 1992, Sequences of Proteins of Immunological Interest, 5th ed. Public Health Service, NIH, Washington D.C.), location of the structural loop regions as defined by Chothia et al. (see, e.g., Chothia et al., Nature 342:87T-883, 1989), a compromise between Kabat and Chothia using Oxford Molecular's AbM antibody modeling software (now Accelrys®, see, Martin et al., 1989, Proc. Natl Acad Sci USA. 86:9268; and world wide web site www(dot)bioinf-org(dot)uk/abs), available complex crystal structures as defined by the contact definition (see MacCallum et al., J. Mol. Biol. 262:732-745, 1996) and the "conformational definition" (see, e.g., Makabe et al., Journal of Biological Chemistry, 283:11564166, 2008).

As used herein, the "variable regions" and "CDRs" may refer to variable regions and CDRs defined by any approach known in the art, including combinations of approaches.

Methods of generating antibodies (i.e., monoclonal and polyclonal) are well known in the art. Antibodies may be generated via any one of several methods known in the art, which methods can employ induction of in vivo production of antibody molecules, screening immunoglobulin libraries or panels of highly specific binding reagents as disclosed [Orlandi D. R. et al. (1989) Proc. Natl. Acad. Sci. 86:3833-3837, Winter G. et al. (1991) Nature 349:293-299] or generation of monoclonal antibody molecules by continuous cell lines in culture. These include but are not limited to, the hybridoma technique, the human B-cell hybridoma technique, and the Epstein-Bar-Virus (EBV)-hybridoma technique [Kohler G., et al. (1975) Nature 256:495-497, Kozbor D., et al. (1985) J. Immunol. Methods 81:31-42, Cote R. J. et al. (1983) Proc. Natl. Acad. Sci. 80:2026-2030, Cole S. P. et al. (1984) Mol. Cell. Biol. 62:109-120].

In cases where the invention compounds are too small to elicit a strong immunogenic response, such antigens (haptens) can be coupled to antigenically neutral carriers such as keyhole limpet hemocyanin (KLH) or serum albumin [e.g., bovine serum albumin (BSA)] carriers (see U.S. Pat. Nos. 5,189,178 and 5,239,078). Coupling to carrier can be effected using methods well known in the art; For example, direct coupling to amino groups can be effected and optionally followed by reduction of imino linkage formed. Alternatively, the carrier can be coupled using condensing agents such as dicyclohexyl carbodiimide or other carbodiimide dehydrating agents. Linker compounds can also be used to effect the coupling; both homobifunctional and heterobifunctional linkers are available from Pierce Chemical Company, Rockford, Ill. The resulting immunogenic complex can then be injected into suitable mammalian subjects such as mice, rabbits, and the like. Suitable protocols involve repeated injection of the immunogen in the presence of adjuvants according to a schedule which boosts production of antibodies in the serum. The titers of the immune serum can readily be measured using immunoassay procedures which are well known in the art.

The antisera obtained can be used directly or monoclonal antibodies may be obtained as described hereinabove.

Antibody fragments can be obtained using methods well known in the art. (See for example, Harlow and Lane, Antibodies: A Laboratory Manual, Cold Spring Harbor Laboratory, New York, 1988, incorporated herein by reference). For example, antibody fragments according to the present invention can be prepared by proteolytic hydrolysis of the antibody or by expression in $E.\ coli$ or mammalian cells (e.g. Chinese hamster ovary cell culture or other protein expression systems) of DNA encoding the fragment.

Alternatively, antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R., Biochem. J., 73: 119-126, 1959. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of $V_H$ and $V_L$ chains. This association may be noncovalent, as described in Inbar et al., Proc. Nat'l Acad. Sci. USA 69:2659-62, 1972. Alternatively, the variable chains can be linked by an intermolecular disulfide bond or cross-linked by chemicals such as glutaraldehyde. Preferably, the Fv fragments comprise $V_H$ and VL chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as $E.\ coli$. The recombinant host cells synthesize a single polypeptide chain with a linker peptide bridging the two V domains. Methods for producing sFvs are described, for example, by Whitlow and Filpula, Methods, 2: 97-105, 1991; Bird et al., Science 242:423-426, 1988; Pack et al., Bio/Technology 11:1271-77, 1993; and Ladner et al., U.S. Pat. No. 4,946,778.

CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry, Methods, 2: 106-10, 1991.

It will be appreciated that for human therapy or diagnostics, humanized antibodies are preferably used. Humanized forms of non-human (e.g., murine) antibodies are chimeric molecules of immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will include at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Thus, according to another aspect of the present invention there is provided an isolated polynucleotide encoding at least one CDR amino acid sequence selected from the group consisting of SEQ ID NOs: 3, 4, 5, 6, 7 and 8. The polynucleotide may encode the CDRs of the light chain (e.g. SEQ ID NOs: 3-5) and/or CDRs of the heavy chain (e.g. SEQ ID NOs: 6-8). Optionally, the polynucleotide may encode each of the CDRs of the antibody. The polynucleotide may further encode sequences which encode for the antibody backbone (e.g. IgG1, 2, 3, or 4). The backbone may comprise human sequences.

The polynucleotide of some embodiments of the invention can be used, preferably cloned into a nucleic acid construct of some embodiments of the invention, for genetically directing the production of the antibodies or antibody chains in the transformed host cell of some embodiments of the invention.

The polynucleotide of some embodiments of the invention can be introduced into cells by any one of a variety of known methods within the art. Such methods can be found generally described in Sambrook et al., [Molecular Cloning: A Laboratory Manual, Cold Springs Harbor Laboratory, New York (1989, 1992)]; Ausubel et al., [Current Protocols in Molecular Biology, John Wiley and Sons, Baltimore, Md. (1989)]; Chang et al., [Somatic Gene Therapy, CRC Press, Ann Arbor, Mich. (1995)]; Vega et al., [Gene Targeting, CRC Press, Ann Arbor Mich. (1995)]; Vectors [A Survey of Molecular Cloning Vectors and Their Uses, Butterworths, Boston Mass. (1988)] and Gilboa et al. [Biotechniques 4 (6): 504-512 (1986)] and include, for example, stable or transient transfection, lipofection, electroporation and infection with recombinant viral vectors.

Also contemplated by the present invention are cells which express the polynucleotides described herein.

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; 5,661, 016, and in the following scientific publications: Marks et al., Bio/Technology 10, 779-783 (1992); Lonberg et al., Nature 368 856-859 (1994); Morrison, Nature 368 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995).

Once antibodies are obtained, they may be tested for metalloenzyme inhibitory activity and affinity. Appropriate assay conditions for metalloprotein inhibition activity are described in Knight et al., FEBS Letters 296(3):263-266 (1992), Cawston et al., Anal. Biochem, 99:340-345 (1979), Cawston et al., Methods in Enzymology 80:771 et seq. (1981); Cawston et al., Biochem. J., 195:159-165 (1981), Weingarten et al., Biochem. Biophys. Res. Comm., 139: 1184-1187 (1984) and U.S. Pat. Nos. 4,743,587 and 5,240, 958.

The inhibitory antibodies of this aspect of the present invention typically have a very high binding affinity and specificity towards MMP-7 with a $K_d$ between 40-50 nM, more typically of about 40-45 nM. The antibodies of this aspect of the present invention typically exhibit a tight binding inhibition pattern towards MMP-7 (e.g. Ki=1-500 nM) and more preferably having a Ki between 100-150 nM), the Ki being at least 2 times, at least 5 times or even at least 10 times lower than the Ki of the antibody towards other MMPs such as MMP2, MMP9 or MMP14.

The antibody may bind to the metal-coordinating ions of the catalytic site and not to the metal ion itself or alternatively the antibody may bind to both the metal ion and its coordinating ions present in the active site pocket. It will be appreciated that the antibody may, in addition to binding to the catalytic site, bind to sites on the surface of MMP-7.

The present invention also provides for any (poly)peptide sequence which comprises at least one, two, three, four, five or six of the CDR sequences of these antibodies as well as homologs and fragments thereof as long as its metalloenzyme inhibitory activity is retained (specific inhibition of the catalytic activity of the metalloprotein).

According to some embodiments of the invention, the antibody may be conjugated to a functional moiety (also referred to as an "immunoconjugate") such as a detectable or a therapeutic moiety. The immunoconjugate molecule can be an isolated molecule such as a soluble and/or a synthetic molecule.

Various types of detectable or reporter moieties may be conjugated to the antibody of the invention. These include, but not are limited to, a radioactive isotope (such as $^{[125]}$ iodine), a phosphorescent chemical, a chemiluminescent chemical, a fluorescent chemical (fluorophore), an enzyme, a fluorescent polypeptide, an affinity tag, and molecules (contrast agents) detectable by Positron Emission Tomagraphy (PET) or Magnetic Resonance Imaging (MRI).

Examples of suitable fluorophores include, but are not limited to, phycoerythrin (PE), fluorescein isothiocyanate (FITC), Cy-chrome, rhodamine, green fluorescent protein (GFP), blue fluorescent protein (BFP), Texas red, PE-Cy5, and the like. For additional guidance regarding fluorophore selection, methods of linking fluorophores to various types of molecules see Richard P. Haugland, "Molecular Probes: Handbook of Fluorescent Probes and Research Chemicals 1992-1994", 5th ed., Molecular Probes, Inc. (1994); U.S. Pat. No. 6,037,137 to Oncoimmunin Inc.; Hermanson, "Bioconjugate Techniques", Academic Press New York, N.Y.

(1995); Kay M. et al., 1995. Biochemistry 34:293; Stubbs et al., 1996. Biochemistry 35:937; Gakamsky D. et al., "Evaluating Receptor Stoichiometry by Fluorescence Resonance Energy Transfer," in "Receptors: A Practical Approach," 2nd ed., Stanford C. and Horton R. (eds.), Oxford University Press, U K. (2001); U.S. Pat. No. 6,350,466 to Targesome, Inc.]. Fluorescence detection methods which can be used to detect the antibody when conjugated to a fluorescent detectable moiety include, for example, fluorescence activated flow cytometry (FACS), immunofluorescence confocal microscopy, fluorescence in-situ hybridization (FISH) and fluorescence resonance energy transfer (FRET).

Numerous types of enzymes may be attached to the antibody of the invention [e.g., horseradish peroxidase (HPR), beta-galactosidase, and alkaline phosphatase (AP)] and detection of enzyme-conjugated antibodies can be performed using ELISA (e.g., in solution), enzyme-linked immunohistochemical assay (e.g., in a fixed tissue), enzyme-linked chemiluminescence assay (e.g., in an electrophoretically separated protein mixture) or other methods known in the art [see e.g., Khatkhatay M I. and Desai M., 1999. J Immunoassay 20:151-83; Wisdom G B., 1994. Methods Mol Biol. 32:433-40; Ishikawa E. et al., 1983. J Immunoassay 4:209-327; Oellerich M., 1980. J Clin Chem Clin Biochem. 18:197-208; Schuurs A H. and van Weemen B K., 1980. J Immunoassay 1:229-49).

The affinity tag (or a member of a binding pair) can be an antigen identifiable by a corresponding antibody [e.g., digoxigenin (DIG) which is identified by an anti-DIG antibody) or a molecule having a high affinity towards the tag [e.g., streptavidin and biotin]. The antibody or the molecule which binds the affinity tag can be fluorescently labeled or conjugated to enzyme as described above.

Various methods, widely practiced in the art, may be employed to attach a streptavidin or biotin molecule to the antibody of the invention. For example, a biotin molecule may be attached to the antibody of the invention via the recognition sequence of a biotin protein ligase (e.g., BirA) as described in the Examples section which follows and in Denkberg, G. et al., 2000. Eur. J. Immunol. 30:3522-3532. Alternatively, a streptavidin molecule may be attached to an antibody fragment, such as a single chain Fv, essentially as described in Cloutier S M. et al., 2000. Molecular Immunology 37:1067-1077; Dubel S. et al., 1995. J Immunol Methods 178:201; Huston J S. et al., 1991. Methods in Enzymology 203:46; Kipriyanov S M. et al., 1995. Hum Antibodies Hybridomas 6:93; Kipriyanov S M. et al., 1996. Protein Engineering 9:203; Pearce L A. et al., 1997. Biochem Molec Biol Intl 42:1179-1188).

Functional moieties, such as fluorophores, conjugated to streptavidin are commercially available from essentially all major suppliers of immunofluorescence flow cytometry reagents (for example, Pharmingen or Becton-Dickinson).

According to some embodiments of the invention, biotin conjugated antibodies are bound to a streptavidin molecule to form a multivalent composition (e.g., a dimmer or tetramer form of the antibody).

Table 1 provides non-limiting examples of identifiable moieties which can be conjugated to the antibody of the invention.

TABLE 1

| Identifiable Moiety | Amino Acid sequence (GenBank Accession No.) | Nucleic Acid sequence (GenBank Accession No.) |
|---|---|---|
| Green Fluorescent protein | AAL33912 | AF435427 |
| Alkaline phosphatase | AAK73766 | AY042185 |
| Peroxidase | CAA00083 | A00740 |
| Histidine tag | Amino acids 264-269 of GenBank Accession No. AAK09208 | Nucleotides 790-807 of GenBank Accession No. AF329457 |
| Myc tag | Amino acids 273-283 of GenBank Accession No. AAK09208 | Nucleotides 817-849 of GenBank Accession No. AF329457 |
| Biotin ligase tag | LHHILDAQKMVWNHR SEQ ID NO: 9 | |
| orange fluorescent protein | AAL33917 | AF435432 |
| Beta galactosidase | ACH42114 | EU626139 |
| Streptavidin | AAM49066 | AF283893 |

As mentioned, the antibody may be conjugated to a therapeutic moiety. The therapeutic moiety can be, for example, a cytotoxic moiety, a toxic moiety, a cytokine moiety and a second antibody moiety comprising a different specificity to the antibodies of the invention.

Non-limiting examples of therapeutic moieties which can be conjugated to the antibody of the invention are provided in Table 2, hereinbelow.

TABLE 2

| Therapeutic moiety | Amino acid sequence (GenBank Accession No) | Nucleic acid sequence (GenBank Accession No) |
|---|---|---|
| Pseudomonas exotoxin | ABU63124 | EU090068 |
| Diphtheria toxin | AAV70486 | AY820132.1 |
| interleukin 2 | CAA00227 | A02159 |
| CD3 | P07766 | X03884 |
| CD16 | NP_000560.5 | NM_000569.6 |
| interleukin 4 | NP_000580.1 | NM_000589.2 |
| HLA-A2 | P01892 | K02883 |
| interleukin 10 | P22301 | M57627 |
| Ricin toxin | EEF27734 | EQ975183 |

The functional moiety (the detectable or therapeutic moiety of the invention) may be attached or conjugated to the antibody of the invention in various ways, depending on the context, application and purpose.

When the functional moiety is a polypeptide, the immunoconjugate may be produced by recombinant means. For example, the nucleic acid sequence encoding a toxin (e.g., PE38KDEL) or a fluorescent protein [e.g., green fluorescent protein (GFP), red fluorescent protein (RFP) or yellow fluorescent protein (YFP)] may be ligated in-frame with the nucleic acid sequence encoding the antibody of the invention and be expressed in a host cell to produce a recombinant conjugated antibody. Alternatively, the functional moiety may be chemically synthesized by, for example, the stepwise addition of one or more amino acid residues in defined order such as solid phase peptide synthetic techniques.

A functional moiety may also be attached to the antibody of the invention using standard chemical synthesis techniques widely practiced in the art [see e.g., hypertexttransferprotocol://worldwideweb(dot)chemistry(dot)org/portal/Chemistry)], such as using any suitable chemical linkage, direct or indirect, as via a peptide bond (when the functional moiety is a polypeptide), or via covalent bonding to an intervening linker element, such as a linker peptide or other chemical moiety, such as an organic polymer. Chimeric peptides may be linked via bonding at the carboxy (C) or amino (N) termini of the peptides, or via bonding to internal chemical groups such as straight, branched or cyclic side chains, internal carbon or nitrogen atoms, and the like. Description of fluorescent labeling of antibodies is provided in details in U.S. Pat. Nos. 3,940,475, 4,289,747, and 4,376,110.

Exemplary methods for conjugating peptide moieties (therapeutic or detectable moieties) to the antibody of the invention are described herein below:

SPDP conjugation—A non-limiting example of a method of SPDP conjugation is described in Cumber et al. (1985, Methods of Enzymology 112: 207-224). Briefly, a peptide, such as a detectable or therapeutic moiety (e.g., 1.7 mg/ml) is mixed with a 10-fold excess of SPDP (50 mM in ethanol); the antibody is mixed with a 25-fold excess of SPDP in 20 mM sodium phosphate, 0.10 M NaCl pH 7.2 and each of the reactions is incubated for about 3 hours at room temperature. The reactions are then dialyzed against PBS. The peptide is reduced, e.g., with 50 mM DTT for 1 hour at room temperature. The reduced peptide is desalted by equilibration on G-25 column (up to 5% sample/column volume) with 50 mM $KH_2PO_4$ pH 6.5. The reduced peptide is combined with the SPDP-antibody in a molar ratio of 1:10 antibody:peptide and incubated at 4° C. overnight to form a peptide-antibody conjugate.

Glutaraldehyde conjugation—A non-limiting example of a method of glutaraldehyde conjugation is described in G. T. Hermanson (1996, "Antibody Modification and Conjugation, in Bioconjugate Techniques, Academic Press, San Diego). Briefly, the antibody and the peptide (1.1 mg/ml) are mixed at a 10-fold excess with 0.05% glutaraldehyde in 0.1 M phosphate, 0.15 M NaCl pH 6.8, and allowed to react for 2 hours at room temperature. 0.01 M lysine can be added to block excess sites. After-the reaction, the excess glutaraldehyde is removed using a G-25 column equilibrated with PBS (10% v/v sample/column volumes).

Carbodiimide conjugation—Conjugation of a peptide with an antibody can be accomplished using a dehydrating agent such as a carbodiimide, e.g., in the presence of 4-dimethyl aminopyridine. Carbodiimide conjugation can be used to form a covalent bond between a carboxyl group of peptide and an hydroxyl group of an antibody (resulting in the formation of an ester bond), or an amino group of an antibody (resulting in the formation of an amide bond) or a sulfhydryl group of an antibody (resulting in the formation of a thioester bond). Likewise, carbodiimide coupling can be used to form analogous covalent bonds between a carbon group of an antibody and an hydroxyl, amino or sulfhydryl group of the peptide [see, J. March, Advanced Organic Chemistry: Reaction's, Mechanism, and Structure, pp. 349-50 & 372-74 (3d ed.), 1985]. For example, the peptide can be conjugated to an antibody via a covalent bond using a carbodiimide, such as dicyclohexylcarbodiimide [B. Neises et al. (1978), Angew Chem., Int. Ed. Engl. 17:522; A. Hassner et al. (1978, Tetrahedron Lett. 4475); E. P. Boden et al. (1986, J. Org. Chem. 50:2394) and L. J. Mathias (1979, Synthesis 561)].

As is mentioned hereinabove, one specific use for an antibody directed against MMP-7 is prevention or treatment of diseases associated with imbalanced or abnormal activity of MMP-7.

Examples of such disease include, but are not limited to, arthritic diseases, such as osteoarthritis (OA), rheumatoid arthritis (RA), septic arthritis, soft tissue rheumatism, polychondritis and tendonitis; metastatic tumors, periodontal diseases; corneal ulceration, such as induced by alkali or other burns, by radiation, by vitamin E or retinoid deficiency; glomerular diseases, such as proteinuria, dytrophobic epidermolysis bullosa; bone resorption diseases, such as osteoporosis, Paget's disease, hyperparathyroidism and cholesteatoma; birth control through preventing ovulation or implantation; angiogenesis relating to tumor growth or to the neovascularization associated with diabetic retinopathy and macular degeneration; coronary thrombosis associated with atherosclerotic plaque rupture; pulmonary emphysema, wound healing and HIV infection.

According to one embodiment the disease is cancer. Exemplary cancers include pancreatic cancer, ovarian cancer, renal cell carcinoma, colon cancer, breast cancer, gastric cancer, rectal cancer and prostate cancer.

The cancer that is treated may be at an early stage or at a late stage. In one embodiment, the cancer has metastasized.

Additional contemplated cancers include, but are not limited to adrenocortical carcinoma, hereditary; bladder cancer; breast cancer; breast cancer, ductal; breast cancer, invasive intraductal; breast cancer, sporadic; breast cancer, susceptibility to; breast cancer, type 4; breast cancer, type 4; breast cancer-1; breast cancer-3; breast-ovarian cancer; Burkitt's lymphoma; cervical carcinoma; colorectal adenoma; colorectal cancer; colorectal cancer, hereditary nonpolyposis, type 1; colorectal cancer, hereditary nonpolyposis, type 2; colorectal cancer, hereditary nonpolyposis, type 3; colorectal cancer, hereditary nonpolyposis, type 6; colorectal cancer, hereditary nonpolyposis, type 7; dermatofibrosarcoma protuberans; endometrial carcinoma; esophageal cancer; gastric cancer, fibrosarcoma, glioblastoma multiforme; glomus tumors, multiple; hepatoblastoma; hepatocellular cancer; hepatocellular carcinoma; leukemia, acute lymphoblastic; leukemia, acute myeloid; leukemia, acute myeloid, with eosinophilia; leukemia, acute nonlymphocytic; leukemia, chronic myeloid; Li-Fraumeni syndrome; liposarcoma, lung cancer; lung cancer, small cell; lymphoma, non-Hodgkin's; lynch cancer family syndrome II; male germ cell tumor; mast cell leukemia; medullary thyroid; medulloblastoma; melanoma, meningioma; multiple endocrine neoplasia; myeloid malignancy, predisposition to; myxosarcoma, neuroblastoma; osteosarcoma; ovarian cancer; ovarian cancer, serous; ovarian carcinoma; ovarian sex cord tumors; pancreatic cancer; pancreatic endocrine tumors; paraganglioma, familial nonchromaffin; pilomatricoma; pituitary tumor, invasive; prostate adenocarcinoma; prostate cancer; renal cell carcinoma, papillary, familial and sporadic; retinoblastoma; rhabdoid predisposition syndrome, familial; rhabdoid tumors; rhabdomyosarcoma; small-cell cancer of lung; soft tissue sarcoma, squamous cell carcinoma, head and neck; T-cell acute lymphoblastic leukemia; Turcot syndrome with glioblastoma; tylosis with esophageal cancer; uterine cervix carcinoma, Wilms' tumor, type 2; and Wilms' tumor, type 1, etc.

According to a particular embodiment, the cancer is pancreatic cancer.

According to a particular embodiment, the pancreatic cancer is a pancreatic adenocarcinoma, a neuroendocrine tumor or an acinar carcinoma of the pancreas.

Thus, the specification provides for a method of treating pancreatic cancer in a subject in need thereof comprising administering to the subject a therapeutically effective amount of an antibody comprising an antigen recognition region which binds a catalytic site of MMP-7, wherein the antibody inhibits the activity of said MMP-7 and wherein the Ki of the antibody towards said MMP-7 is at least 5 times lower than a Ki of the antibody towards MMP2 or MMP9, thereby treating the pancreatic cancer.

Examples of such antibodies are provided herein and WO2012/056455 and WO2010/012167, the contents of which are incorporated herein by reference.

The specificity of the antibodies can be confirmed using assays known in the art. Appropriate assay conditions for metalloprotein inhibition activity are described in Knight et al., FEBS Letters 296(3):263-266(1992), Cawston et al., Anal. Biochem, 99:340-345 (1979), Cawston et al., Methods in Enzymology 80:771 et seq. (1981); Cawston et al., Biochem. J., 195:159-165 (1981), Weingarten et al., Biochem. Biophys. Res. Comm., 139:1184-1187 (1984) and U.S. Pat. Nos. 4,743,587 and 5,240,958.

According to another embodiment the disease is inflammatory bowel diseases (IBD) which are severe gastrointestinal disorders characterized by intestinal inflammation and tissue remodeling, that increase in frequency and may prove disabling for patients. The major forms of IBD, ulcerative colitis (UC) and Crohn's disease are chronic, relapsing conditions that are clinically characterized by abdominal pain, diarrhea, rectal bleeding, and fever.

Subjects which may be treated include mammalian subjects such as humans.

Another use for an antibody directed against MMP-7 is diagnosis of a disease associated with an upregulation of expression of MMP-7.

Thus, according to another aspect of the present invention there is provided a method of diagnosing a disease associated with imbalanced or abnormal activity of MMP-7 in a subject, the method comprising contacting a sample of the subject with an antibody described herein (e.g. GSM-192) so as to analyze expression of MMP-7, wherein an upregulation of expression of the MMP-7 is indicative of the disease associated with imbalanced or abnormal activity of MMP-7.

Methods of analyzing expression of MMP-7 using the disclosed antibody include, but are not limited to Western analysis, immunoprecipitation and immunohistochemistry.

A sample can be a liquid such as urine, saliva, cerebrospinal fluid, blood, serum or the like; a solid or semi-solid such as tissues, feces, or the like; or, alternatively, a solid tissue such as those commonly used in histological diagnosis.

Typically the amount of MMP-7 is compared with a control (a corresponding sample from a healthy subject) or known amounts of MMP-7 which correspond to a healthy subject).

Following the diagnosis, the subject may be informed of the outcome. Further additional diagnostic tests may be carried out on the basis of the outcome of the tests using the MMP-7 antibody disclosed herein.

It will be appreciated that as well as performing the diagnosis in vitro (i.e. on samples of the subject), the diagnosis may also be effected in vivo.

Diseases which may be diagnosed include those listed above for diseases which can be treated.

If the outcome of the diagnosis is negative—i.e. there is no significant increase in the expression of MMP-7, and it is corroborated that the patient has cancer, then chemotherapeutic agents (which are not MMP-7 antibodies) may be prescribed, according to the type of cancer.

If the outcome of the diagnosis is positive—i.e. an increase in expression of MMP-7, the present inventors contemplate treating the disease with an agent that downregulates the amount/activity of MMP-7. In one embodiment, the agent that is used to treat the disease is an inhibitory MMP-7 antibody, such as disclosed herein and in WO2012/056455 and WO2010/012167, the contents of which are incorporated herein by reference.

Methods of generating MMP-7 antibodies are known in the art. In one embodiment, the method includes immunizing a subject (e.g. animal subject) with:

(i) a synthetic zinc mimicry compound having structural and electronic properties similar to a catalytic domain of the MMP-7; and (ii) MMP-7.

Synthetic zinc mimicry compounds having structural and electronic properties similar to a catalytic domain of the metalloenzyme are typically compounds which comprise chelated metal ions. The metal ion is typically Zinc or its analogous ions Cobalt or Cadmium.

According to one embodiment, the chelator is porphyrin.

The zinc mimicry compound may be selected based upon the structural and electronic properties of the actual catalytic domain in the target polypeptide. Typically, the target polypeptide includes 3 amino acids which provide three contact points required for the transition metal coordination. Representative coordination complex geometries can be tetrahedral, square planar or trigonal depending upon the transition metal ion. In general the mimicking compositions of the present invention are selected based upon the amino acid side chain structure and the geometry of coordination. Typically, amino acids which can coordinate transition metal binding are histidine, arginine, glutamate, cysteine, methionine, tryptophan, serine, threonine and tyrosine, with the first two being preferable.

Exemplary synthetic zinc mimicry compounds are disclosed in WO2004/087042 and WO2008/102359, incorporated herein by reference.

According to one embodiment the synthetic zinc mimicry compound has the general Formula (I):

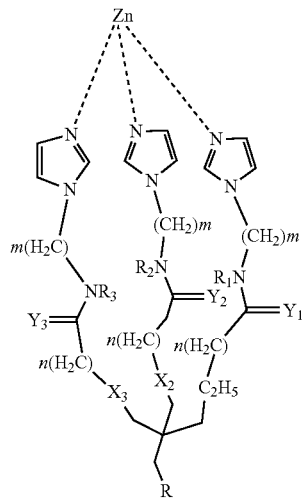

wherein:

m and n are each independently an integer from 1 to 6;
$X_1$-$X_3$ and $Y_1$-$Y_3$ are each independently O or S;
$R_1$-$R_3$ are each independently selected from the group consisting of hydrogen, alkyl, and cycloalkyl; and R is O—($CH_2$)x-C(=O)NR'—($CH_2$)y-NR'R'' whereas:

x and y are each independently an integer from 1 to 6; and R' and R'' are each independently selected from the group consisting of hydrogen, alkyl, and cycloalkyl.

According to a particular embodiment of this aspect of the present invention the compound is [2-(2-minoethylcarbomoyl)-ethoxymethyl]-tris-[2-(N-(3-imidazol-1-yl-propyl))-ethoxymethyl]methane, termed, Imisdp, having the general Formula (II):

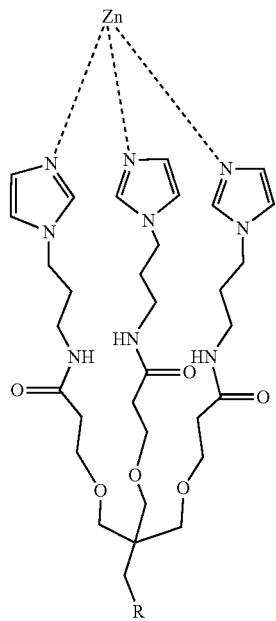

wherein R is O—CH$_2$—CH$_2$—CONH—CH$_2$—CH$_2$—NH$_2$

As mentioned, the method of the present invention is carried out by immunizing with both the zinc mimicry compound described herein above and the MMP-7 metalloenzyme itself.

The present invention contemplates immunization with the full-length MMP-7 or portions thereof. Typically, the portion should contain an antigenic determinant (i.e. epitope) which is specific to MMP-7.

According to one embodiment, the antigenic determinant is on the surface of MMP-7.

The MMP-7 used for immunization may be purified from its in vivo environment or alternatively may be generated through recombinant means.

According to one embodiment, the immunization procedure comprises initial immunization with the zinc mimicry compound and subsequent (e.g. three-twelve weeks later) immunization with MMP-7. The exact time of immunization may be determined by checking to see if an immune response is present in the immunized animal (e.g. mouse). For instance the titre of antibodies in the serum may be analyzed.

According to another embodiment, the immunization procedure comprises initial immunization with MMP-7 and subsequent (e.g. three-twelve weeks later) immunization with the zinc mimicry compound.

According to yet another embodiment, the immunization procedure comprises co-immunization (i.e. at the same time) with both the MMP-7 and the zinc mimicry compound.

The antibodies of the present invention may be administered to the subject per se or as part of a pharmaceutical composition.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the antibody accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Conventional approaches for drug delivery to the CNS include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

The term "tissue" refers to part of an organism consisting of an aggregate of cells having a similar structure and/or a common function. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmonary tissue, gonadal tissue, hematopoietic tissue.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (antibody) effective to prevent, alleviate or ameliorate symptoms of a disorder (e.g., cancer/anthrax infection) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide tissue or blood levels of the active ingredient which are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

The present inventors have shown that the antibody of this aspect of the present invention enhances the sensitivity of chemotherapeutic agents. Thus, the present inventors contemplate administering the antibody with a chemotherapeutic agent.

Examples of chemotherapeutic agents include, but are not limited to Acivicin; Aclarubicin; Acodazole Hydrochloride; Acronine; Adriamycin; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Oxaliplatin; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Taxol; Tecogalan Sodium; Tegafur; Teloxantrone Hydrochloride; Temoporfin; Teniposide; Teroxirone; Testolactone; Thiamiprine; Thioguanine; Thiotepa; Tiazofuirin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride. Additional antineoplastic agents include those disclosed in Chapter 52, Antineoplastic Agents (Paul Calabresi and Bruce A. Chabner), and the introduction thereto, 1202-1263, of Goodman and Gilman's "The Pharmacological Basis of Therapeutics", Eighth Edition, 1990, McGraw-Hill, Inc. (Health Professions Division).

In a particular embodiment, the chemotherapeutic agent is a nucleoside analogue, examples of which include, but are not limited to gemcitabine, methotrexate, 5-fluorouracil, cytosine arabinoside, behenoyl cytosine arabinoside, tegafur, UFT, and the like.

According to a particular embodiment, the nucleotide agent is gemcitabine.

According to a particular embodiment, the chemotherapeutic agent is Oxaliplatin.

In the context of a combination therapy, the chemotherapeutic agent may be administered by the same route of administration (e.g. intrapulmonary, oral, enteral, etc.) as the antibody is administered. In the alternative, the chemotherapeutic agent may be administered by a different route of administration to the antibody.

The chemotherapeutic agent can be administered immediately prior to (or after) the antibody, on the same day as, one day before (or after), one week before (or after), one month before (or after), or two months before (or after) the antibody, and the like.

The chemotherapeutic agent and the antibody can be administered concomitantly, that is, where the administering for each of these reagents can occur at time intervals that partially or fully overlap each other. The chemotherapeutic agent and the antibody can be administered during time intervals that do not overlap each other. For example, the chemotherapeutic agent can be administered within the time frame of t=0 to 1 hours, while the antibody can be administered within the time frame of t=1 to 2 hours. Also, the chemotherapeutic agent can be administered within the time frame of t=0 to 1 hours, while the antibody can be administered somewhere within the time frame of t=2-3 hours, t=3-4 hours, t=4-5 hours, t=5-6 hours, t=6-7 hours, t=7-8 hours, t=8-9 hours, t=9-10 hours, and the like. Moreover, the antibody can be administered somewhere in the time frame of t=minus 2-3 hours, t=minus 3-4 hours, t=minus 4-5 hours, t=5-6 minus hours, t=minus 6-7 hours, t=minus 7-8 hours, t=minus 8-9 hours, t=minus 9-10 hours.

The antibody of the present invention and the chemotherapeutic agent are typically provided in combined amounts to achieve therapeutic, prophylactic and/or pain palliative effectiveness. This amount will evidently depend upon the particular compound selected for use, the nature and number of the other treatment modality, the condition(s) to be treated, prevented and/or palliated, the species, age, sex, weight, health and prognosis of the subject, the mode of administration, effectiveness of targeting, residence time, mode of clearance, type and severity of side effects of the pharmaceutical composition and upon many other factors which will be evident to those of skill in the art. The antibody will be used at a level at which therapeutic, prophylactic and/or pain palliating effectiveness in combination with the chemotherapeutic agent is observed.

The chemotherapeutic agent may be administered (together with the antibody) at a gold standard dosing as a single agent, below a gold standard dosing as a single agent or above a gold standard dosing as a single agent.

According to specific embodiments, the chemotherapeutic agent is administered below the gold standard dosing as a single agent.

As used herein the term "gold standard dosing" refers to the dosing which is recommended by a regulatory agency (e.g., FDA), for a given tumor at a given stage.

According to other specific embodiments, the chemotherapeutic agent is administered at a dose that does not exert at least one side effect which is associated with the gold standard dosing. Non-limiting examples of side effects of a chemotherapeutic agent treatment include skin rash, diarrhea, mouth sores, paronychia, fatigue, hyperglycemia, hepatotoxicity, kidney failure, cardiovascular effects, electrolytes anomalies and GI perforations.

Thus, in one embodiment, the amount of the chemotherapeutic agent is below the minimum dose required for therapeutic, prophylactic and/or pain palliative effectiveness when used as a single therapy (e.g. 10-99%, preferably 25 to 75% of that minimum dose). This allows for reduction of the side effects caused by the chemotherapeutic agent but the therapy is rendered effective because in combination with the antibody, the combinations are effective overall.

In one aspect of the present invention, the antibody and the chemotherapeutic agent are synergistic with respect to their dosages. That is to say that the effect provided by the antibody of the present invention is greater than would be anticipated from the additive effects of the chemotherapeutic agent and the antibody when used separately. In an alternative embodiment, the chemotherapeutic agent of the present invention and the antibody are synergistic with respect to their side effects. That is to say that the side-effects caused by the antibody in combination with the chemotherapeutic agent are less than would be anticipated when the equivalent therapeutic effect is provided by either the chemotherapeutic agent or antibody when used separately.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein, the term "preventing" refers to keeping a disease, disorder or condition from occurring in a subject who may be at risk for the disease, but has not yet been diagnosed as having the disease.

As used herein, the term "subject" includes mammals, preferably human beings at any age which suffer from the pathology. Preferably, this term encompasses individuals who are at risk to develop the pathology.

The terms "comprises", "comprising", "includes", "including", "having" and their conjugates mean "including but not limited to".

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y.

(1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Antibody generation and purification: Female BALB/c mice were immunized with complete Freund's adjuvant (Disco) and 30 μg of the catalytic domain of MMP-7 or Zn Tripod-KLH and boosted every 2 weeks with incomplete Freund's adjuvant by subcutaneous injection. Spleens were collected, and B cells were fused with NSO murine myeloma cells. Hybridomas were screened with ELISA for immunoreactivity against the catalytic domain of MMP-7 and Zn Tripod, and selected hybridomas were subcloned and expanded in tissue culture. Hybridoma cells of GSM-192 were grown in DCCM (serum-free medium designed for hybridoma cell growth and monoclonal antibody production, purchased from Biological Industries, Israel). Cells were precipitated by centrifugation at 193×3 g, and the supernatant was collected. The supernatant was dialyzed against 20 mM phosphate buffer (pH 8). A 1 ml HiTrap protein A high performance column was equilibrated with 100 mM phosphate buffer (pH 8), and the supernatant was loaded at 1 ml/min. The antibody was eluted with 100 mM citrate buffer (pH 6) and dialyzed against 50 mM Tris (pH 7.5) and 150 mM NaCl.

A dot blot was performed by immobilizing 1, 1.5 and 2 μg zymogen and activated MMP-7 recombinant enzyme on nitrocellulose membrane pre wetted with TBST using a vacuum based manifold 96 well dot-blot system (GE 10447900 Minifold dot blot). The blocking was performed for 1 hour at room temperature with 3% BSA in TBST. The membrane was then probed for binding by antibody eluted in the earlier step by incubating overnight. The anti MMP-7 mAb used was at 2 ug/ml concentration in TBST. The membrane after 3 washes in TBST was incubated with goat anti mouse HRP antibody and developed using ECL to determine the selectivity of binding towards catalytic form only.

Antibody digestion with papain for Fab generation. Papain was activated in 0.5 M Tris-HCl (pH 8), 10 mM EDTA, and 5 mM dithiothreitol for 15 min at 37° C. Active papain was added to a solution of intact GSM-192 at a ratio of 1:1,000, and the digestion process was carried out for 3 h at 37° C. The digestion reaction was terminated with the addition of 20 mM iodoacetamide in the dark at room temperature for 30 min. The Fab fragment was isolated from the Fc by a protein A column, and the Fab fragment was collected from the flow-through and dialyzed against 50 mM Tris (pH 7.5) and 150 mM NaCl. The purity of the Fab fragment was estimated by 12% SDS-PAGE gel.

MMP-7 Elisa binding assay: A 96-well plate (Nunc) was coated with MMP at 5 mg/ml. After coating, the plate was incubated with the GSM-192 at 25° C. for 1 h. The bound Fab fragment/full length was detected using a goat anti-Fab/anti-mouse antibody followed by peroxidase-conjugated bovine anti-goat antibody according to standard procedures. A four-parametric sigmoidal curve-fitting analysis was used to calculate the half-maximal effective concentration.

MMP-7 enzymatic kinetic assay: The enzymatic activity of MMP-7 in the presence of GSM-192 Fab was measured at 37° C. by monitoring the hydrolysis of fluorogenic peptide Mca-Pro-Leu-Gly-Leu-Dpa-Ala-Arg-NH2 (SEQ ID NO: 10) at λex=340 nm and GSM-192=390 nm as described previously[30]. A range of different concentrations of GSM-192 Fab (0-200 nM) were incubated with 10 nM of MMP-7 in 50 mM Tris-HCl buffer (pH 7.5 at 37° C.), 100 mM NaCl, 5 mM CaCl2, and 0.05% Brij-35 for 2 h at 37° C. The enzymatic reaction was initiated by addition of the fluorogenic peptide to a final concentration of 10 μM. Fluorescence was recorded immediately and continuously for 30 min.

Initial reaction rates were measured, and the inhibition constant was evaluated by fitting the data to the equation where Vi is initial velocity in the presence of the inhibitor, VO is the initial velocity in the absence of inhibitor, and I is the inhibitor concentration. To determine the type of inhibition, the initial velocity of MMP-7 was measured as a function of substrate concentration (0-30 mM) at several fixed concentrations of the Fab GSM-192 (between 0-500 nM). The values of apparent KM and Vmax were derived by linearization.

$$\frac{Vi}{Vo}\% = \frac{1}{1 + \frac{[I]}{IC50}} \times 100$$

Antibody Sequencing: Immunoglobulin V region genes were cloned and sequenced after amplification by PCR. The total RNA was prepared from 5×10$^6$ hybridoma cells by the phenol-guanidine isothiocyanate method (peqGOLD TriFast of peqlab biotechnologie), according to the manufacturer's protocol. CDNA was obtained, and amplification was performed, in one step using ReverseiT™ one step RT-PCR Kit (ABgene). V region genes were amplified by using degenerate sense primers, homologous to the mouse heavy and light chain leader sequences and antisense constant primers (Amersham Biosciences). The amplification products were ligated into the pGEM-T Easy Vector (Promega) by using standard protocols, and both strands of inserts were sequenced on an automated sequencer at the DNA sequencing unit (Biological Services, Weizmann Institute of Science).

GSM-192 Light Chain Sequence (SEQ ID NO: 1)

DIVTQSPASLAVSLGQRATISCRASESFDSYGNTFVHWYQQKP

GQPPKLLIYLVSNLESGVPAGFRGRGSRTDFTLTIDPVEADDA

ATYYCQQNNEDPYTFGGGTKLEIKRA

GSM-192 Heavy Chain Sequence (SEQ ID NO: 2)

EVQLQQSGPELVKPGASVKIPCKASGYTFTDYNMDWMKQSHG

KSLEWIGHINPNNGGTFYNQKFKDKATFIVDKSSNTAYMELRS

LTSEDTAVYFCARGGGLRRGPFAYWGQGTLVTVS

Protein crystallography of GSM-192 Fab: The crystals of free GSM-192 Fab obtained using the hanging drop vapor diffusion method diffracted at best to 2.3 Å resolution. The crystals were grown from 0.2 M CaCl2, 0.1M HEPES pH=7, 20% PEG 6000 and 0.01M Betaine hydrochloride. The crystals formed in the trigonal space group P3121, with cell constants a, b=88.44, and c=119.34 Å and g=120° with one copy of the light and heavy chains. A full X-ray data set to 2.3 Å resolution was collected at 100 K using an RU-H3R rotating anode with an RAXIS IV++ detector. The diffraction images were indexed and integrated using the HKL2000 program[31]. Processing of X-ray diffraction data collected in oscillation mode and the integrated reflections was scaled using the SCALEPACK program[31,39]. Structure factor amplitudes were calculated using TRUNCATE from the CCP4 program suite. Details of the data collection are also described in Table 3. The structure was solved by molecular replacement with the program PHASER[41], using the refined structure of the Anti-Abeta monoclonal antibodies mAbs (PFA1) (Protein Data Bank (PDB) accession code 2IPU) as a model. All steps of atomic refinements were carried out with the PHENIX program[42]. The model was built into 2mFobs—DFcalc, and mFobs—DFcalc maps by using the COOT program[43]. Refinement weights were optimized. The GSM-192 Fab construct is composed of 224 amino acid residues in the heavy chain and 215 amino acids in the light chain (439 residues). The final model includes residues 1-221 in the heavy chain and 2-185 in the light chain. The Rfree value is 27.85% (for the 5% of reflections not used in the refinement), and the Rwork value is 23.22% for all data to 2.3 Å. The GSM-192 Fab model was evaluated with the PROCHECK program[44]. Details of the refinement statistics of the GSM-192 Fab structure are described in Table 3. The coordinates and structure factors for GSM-192 Fab have been deposited in the PDB under the ID code 6FBJ.

TABLE 3

| Data collection | |
| --- | --- |
| Resolution range (Å) | 50.0-2.30 (2.34-2.30)[a] |
| Space group | P3$_1$21 |
| Unit cell dimensions | |
| a, b, c (Å) | 88.44, 88.44, 119.34 |
| γ (°) | 120 |
| Number of molecules in the asymmetric unit | 1 |
| Number of reflections measured | 870,771 |
| Number of unique reflections | 24,579 (1,203)[a] |
| R$_{sym}$ | 0.085 (0.58)[a] |

TABLE 3-continued

| | |
| --- | --- |
| Completeness (%) | 100.0 (100.0)[a] |
| Redundancy | 12.0 (11.9)[a] |
| <I>/<σ(I)> | 33.0 (5.2)[a] |
| Refinement statistics | |
| Resolution (Å) | 38.3-2.30 |
| Rwork (%) | 23.22 |
| Rfree (%) | 27.85 |
| B-factor (Å$^2$) | |
| protein | 37.7 |
| RMSD from ideal geometry | |
| rmsd bond length (Å) | 0.009 |
| rmsd bond angles (°) | 1.2 |
| Ramachandran plot (%) | |
| Most favored | 85.8 |
| Additional favored | 13.3 |
| Generously allowed | 0.0 |
| Disallowed regions | 0.9 |

[a]Values in parentheses correspond to the highest-resolution shell

Computational modeling and docking: The Fv domains of antibody GSM-192 were computationally docked to MMP-7. Comparison of the several structures of MMP-7 available in the PDB showed variations in the structure, which affected the width of the active site cleft. Normal modes analysis[45], applied to the experimental structures, showed similar mobility of the loops. Therefore the experimental structures and several normal modes conformers of MMP-7 were used in docking. The molecules were docked using the FFT-based geometric-electrostatic-hydrophobic (GEH) version of MolFit[46-48], which executes an exhaustive step-wise scan of the relative rotations and translations of the docked molecules and provides a GEH score for every tested position. The resultant poses were filtered using a post-scan propensity and solvation (P&S) filter[49].

The filtered models were further screened to include only models where the interaction involves exposed residues in the antibody CDRs. This screen counted the number of atomatom contacts (≤5 Å distance) between exposed CDR residues and the target molecule. The GEH score of MolFit is sensitive to small changes in the relative orientation of the molecules[50] and local rigid-body refinements were previously found to be very effective for identifying genuinely high-scoring docking models. Therefore, the models from the several scans were refined, by allowing small local rotations in steps of 2°. The refinement highlighted one model in the docking results. This model was ranked 1 in the docking scan that employed a normal modes conformer closely resembling structure 2y6a and its refined score was 3.1σ above the next model and 9σ above the mean score (mean score and σ were determined by fitting an extreme value distribution function to the distribution of GEH scores[50]). Notably, the same model was obtained in scans that included AHA as part of the MMP-7 structure and scans without AHA. In the latter case, the location of AHA was empty and accessible.

Anchoring spots was used to identify preferred binding locations of single amino acid side chains on the surface of proteins. The mapping was performed with ANCHORSmap[32]. UCSF-Chimera[51] was used for structure analyses and comparisons and for producing FIGS. 3A-D.

Cell culture: All cell lines were kept in a humidified incubator at 37° C. with 5% CO2 and cultured in complete media consisting of DMEM, RPMI medium 1640 or IMDM supplemented with 10% fetal calf serum, 1% penicillin/streptomycin, 1% L-glutamine, 1% sodium pyruvate.

MMP-7 lentiviral silencing and FACS analysis: Stable knockdown of MMP-7 in AsPC-1 pancreatic cancer cells was achieved by HIV-based stable transduction with shRNA against MMP-7 using the ViraPower Lentiviral Expression System (Thermo Fisher Scientific) in combination with commercially available shRNA oligos (Sigma Aldrich). Recombinant retrovirions were generated according to standard protocols[52]. AsPC-1 cells were transduced at an MOI of 10 in the presence of 8 µg/ml polybrene. In 48 h post transduction, AsPC-1 cell were passaged and allowed to adhere for 6 h before 40 µg/ml puromycin was added to positively select transduced cells. Antibiotic pressure was maintained until 24 h after 100% of non-transduced control cells maintained at identical conditions were killed. Knockdown efficacy was determined by qRT-PCR. RNA was isolated from cells using TRIzol (Life Technologies) according to the manufacturer's protocols. Reverse transcription was performed using the High Capacity RT Kit (Life technologies) according to the manufacturer's instructions. Cell cycle analysis using propidium iodide in FACS was done on the stable knockdown cells maintained at 80% confluency.

MTT Cell proliferation assay: MTT solutions (M5655 SIGMA) was added at 10% of total culture volume (0.5 mg/ml MTT in RPMI/IMDM without phenol red) and after 3 hours incubation, plate was washed with PBS and solubilized using MTT solvent (0.1 N HCl in anhydrous isopropanol). The read out was obtained at 630-690 nm wavelengths in the spectrophotometer plate reader. Relative percentage of cell proliferation was determined in comparison to the control wells. A curve fitting analysis for $IC_{50}$ was performed using Origin software v8.5.

FACS Annexin-V apoptosis detection assay: 70% confluent cells in 6 cm plates were treated with sterile GSM-192 Fab fragment/control anti LOXL-2 Fab fragment for 24 h and prepared for FACS using the Annexin-V FITC apoptosis detection kit (E Biosciences 88-8005-72) as described previously[53]. The FACS acquisition was done using FACS LSR-II machine in Cell Quant software (Becton Dickinson) and further analysis on FlowJo software (Treestar, Inc., San Carlos, Calif.).

Western Blots: Treated cells were lysed with RIPA buffer containing protease inhibitors and shaken intermittently while stored in ice for 30 min. The debris was removed by centrifugation at 14,000×g and supernatant was used for BCA protein determination assay. Alternatively, culture supernatants were concentrated at least 10 times using 0.2 µm centricons. Once normalized to equal protein content, sample buffer was added and heated for 3 minutes at 95° C. The denatured samples were centrifuged for 5 min at 14,000×g before 25 µL was loaded onto SDS page gel and standard blotting procedures were followed (General Protocol for Western Blotting, BioRad bulletin 6376). Primary Abs used were MMP-7 (abcam, ab5706), Fas-L (abcam, ab15285), α Tubulin Ab (sc31779).

Wound Healing Assay (Scratch Assay): The migratory behavior of cells was assayed by means of a wound-healing assay using a culture-insert (ibidi GmbH, Am Klopferspitz 19, Martinsried, Germany) according to the manufacturer's instruction. After 24 h the culture-inserts were removed leaving a cell-free gap ("defined as a wound") of approx. 500 µm. The migration rate into this "wound area" was documented and measured using Carl Zeiss microscope (DeltaVision Microscopy Imaging Systems—GE Healthcare Life Sciences, USA). The migration rate was determined by percentage area covered by cells. Each analysis was performed in triplicates and was repeated two times.

Trans-well migration assay: Cells were starved overnight in assay media (IMDM media containing only 1% serum). Cells (1×10⁵) were added to the top chambers of 24-well transwell plates (BD Biosciences; 8 µm pore size), and assay media, with or without GSM-192, was added to both chambers. After overnight incubation, cells that failed to migrate on top well were removed, and the cells that migrated to the bottom were fixed with 4% PFA and stained with crystal violet (0.05%). The numbers of cells in five fields were counted under 20× magnification, and the mean for each chamber determined.

Immunohistochemistry: Frozen human PDAC sections in OCT (10 µm thick) were cut on a cryostat. Sections were dried on bench top for 30 min at room temperature, rehydrated in PBS for 10 min, preincubated with PNB blocking buffer (PerkinElmer Life Sciences) for 1 h at room temperature, and then incubated with the primary antibody of interest, GSM-192 mAb or MMP-7 (abcam, ab5706) overnight at 4° C. The corresponding secondary HRP antibodies were used at manufacturer's recommended dilution. The slides were mounted in mounting medium. The images of mounted sections were obtained using Carl Zeiss optical microscope.

Animal Models

RIP1-Tag2: The RIP1Tag2 (RT2) murine PanNET model was developed by the fusion of Rat Insulin II promoter region to the SV40 early region that encodes the large T and small t antigens. Although oncogene expression begins during embryonic development (E8.5), the pancreatic islets initially have a normal anatomical and histological appearance ("normal" stage). Beginning at 4-5 weeks of age, hyperplastic and dysplastic islets begin to appear, rending 50% of all islets by 10 weeks of age. Angiogenic islets appear beginning around 6 weeks of age, and represent 10% of all islets at 10.5 weeks. Angiogenic islets are recognized by their dilated blood vessels and micro-hemorrhages. Tumors form beginning at 9-10 weeks and represent 2-4% of all the islets by 14 weeks. About half of the tumors at end stage evidence either focal or widespread invasion to the surrounding acinar tissue. RIP-Tag2 mice die at approximately 14 weeks of age primarily due to hyperinsulinemia. Additionally, a RIP1-Tag2-Vecad-tdTomato mouse was used to demonstrate the collapse of the blood vessels postmortem (n=1), and RIP1-Tag2-CX3CR1 to visualize the macrophages in the tumor capsule (n=1).

Gemcitabine co-treatment: 10,000 AsPC-1 cells/well were seeded into 96 well flat bottom plate and incubated overnight at in a humidified incubator at 37° C. with 5% CO2. Media in wells were replaced by serum free RPMI medium containing 2.33 µM GSM-192 or PBS and 0.05, 0.1, 0.5, 1, 5, 10, 40 and 80-µM gemcitabine. The plates were further incubated for 72 hours in a humidified incubator at 37° C. with 5% CO2. MTT solutions (M5655 SIGMA) was added at 10% of total culture volume (0.5 mg/ml MTT in RPMI/IMDM without phenol red) and after 3 hours incubation, plate was washed with PBS and solubilized using MTT solvent (0.1 N HCl in anhydrous isopropanol). The read out was obtained at 650 nm wavelength in the spectrophotometer plate reader and the background read out was performed at 570 nm. Cell death data was plotted as a function of the log of Gemcitabine concentration and fitted on a variable slope sigmoidal regression model (GraphPad prism 8.3.0). Further, an average of $IC_{50}$ from 3 experimental repeats and corresponding standard deviation was calculated.

Statistics: For all representative results, experiments were repeated at least 2 times and replicates were used to calculate the s.e.m. Normally distributed data were tested by Student's 1-tests with unequal variances to compare continuous variables between two groups. Statistical analysis was performed using GraphPad Prism 7.

Data availability: GSM-192 X-ray structure was deposited in the protein data bank with accession number 6DBJ.

Results

Figure 1A:
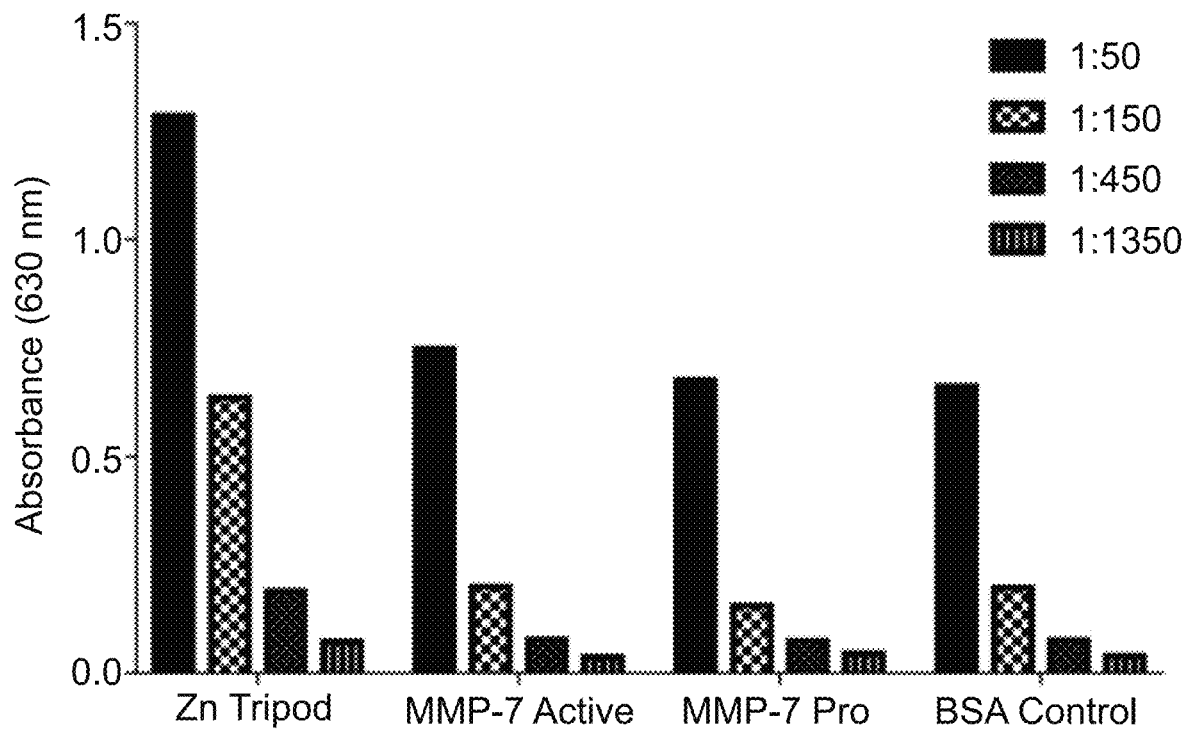
FIGS. 1A-B. Immunization with synthetic Zn Tripod or human MMP-7 catalytic enzyme alone did not yield antibody candidates specifically binding the activated enzyme. A, Immune responses were examined in serum using ELISA against antigens Zn-Tripod-KLH (Zn Tripod), MMP-7 activated form, MMP-7 zymogen/pro form and BSA control in bleed from mouse immunized with Zn Tripod alone. The graph shows binding with various antigen dilutions. The ELISA did not show presence of antibodies binding MMP-7 activated conformation or zymogen forms. Reactivity towards Zn Tripod was observed. B, Immune responses were also checked in ELISA using bleed from mouse immunized with recombinant human MMP-7 activated form alone. The weak response was characterized by binding towards both MMP-7 pro form and MMP-7 activated form. Notably no binding was observed in Zn Tripod coated wells.
Figure 1B:
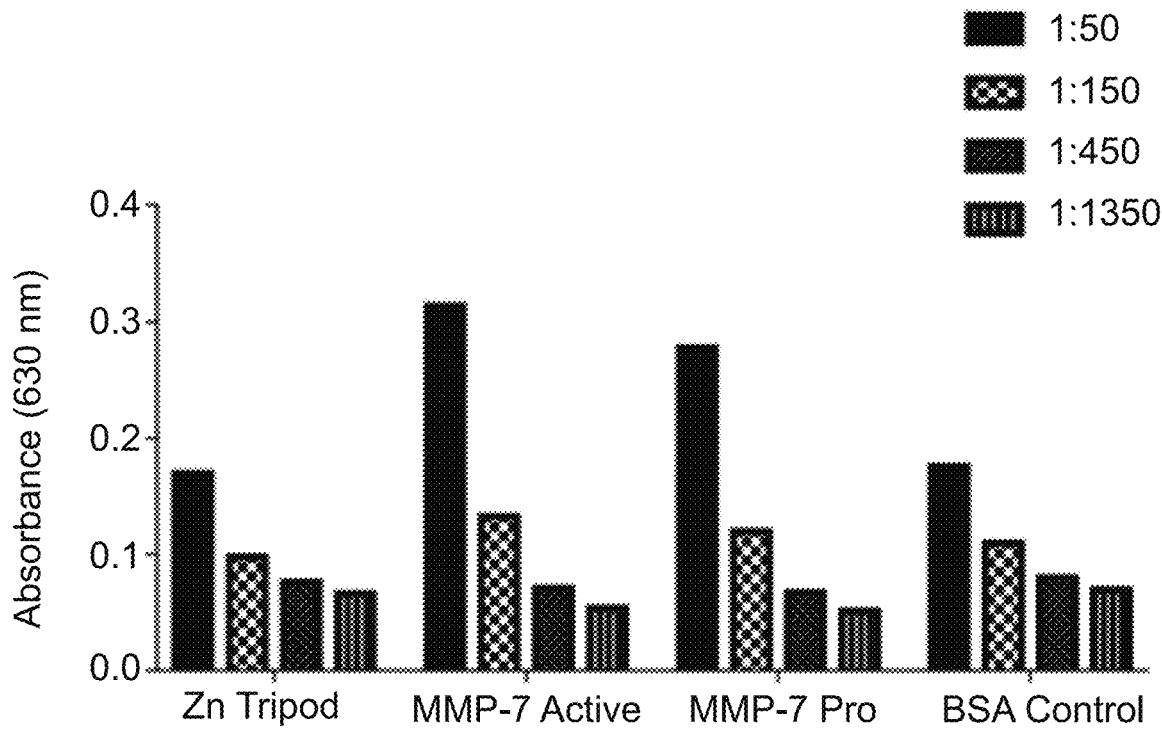

Individual immunization with Zn Tripod or activated recombinant human MMP-7 did not yield conformation selectivity: The conserved structure of the metalloenzyme MMP-7 contains catalytic zinc-histidine complex, residing within the enzyme active site. Immunization of Female BALB/c mice with repeated doses small synthetic Zn Tripod-KLH emulsified with complete Freund's adjuvant alone did not result in anti-MMP-7 antibodies (FIG. 1A) and similar immunization with MMP-7 activated enzyme alone also did not result in affinity maturated antibodies with unique specificity towards the this form of the enzyme (FIG. 1B). The anti-Zn Tripod, anti-MMP-7 immune responses were examined respectively in mouse serum using direct enzyme linked immune sorbent assay (ELISA). These two immunizations failed to show either cross reactivity or conformational selectivity. These results highlighted the limitation in generating affinity maturation in vivo using individual immunization with active site mimicry molecule (Zn Tripod) or with the traditional approach using activated enzyme to generate antibodies of interest.

Figure 2A:
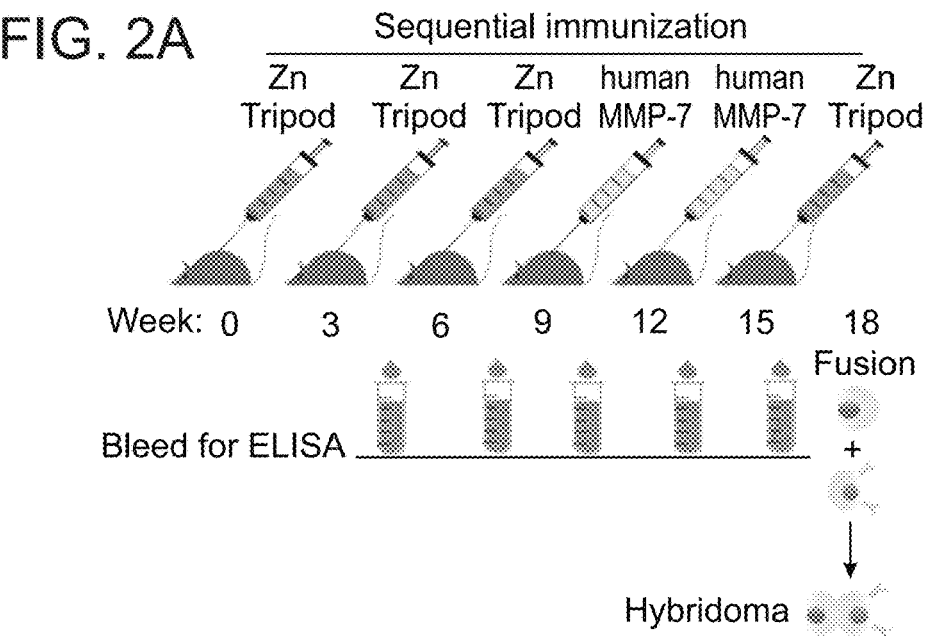
FIGS. 2A-F. Alternate immunization yields anti MMP-7 antibody with high binding affinity and selectivity towards the activated form of the enzyme. A, Female BALB/c mice were immunized in 3 week intervals with synthetic Zn Tripod emulsified with complete Freund's adjuvant or activated form of recombinant human MMP-7. Progressive immune responses were observed as a function of repetitive injection using an ELISA. B cells from candidates with high binding affinity were selected for hybridoma generation at week 18. B, Serum immune response of selected mouse prior to fusion when examined using ELISA showed bi-specificity towards both Zn Tripod and MMP-7 and showed negligible binding with MMP-14 at various dilutions. C, Purified hybridoma monoclonal antibody GSM-192 binding curve with MMP-7 active enzyme (Kd=43.1±1.43 nM). The antibody did not bind effectively to a panel of other MMPs indicating its high specificity towards MMP-7. D, The effect of GSM-192 Fab on the enzymatic activity of human MMP-7 was examined in vitro using short fluorogenic peptides. GSM-192 Fab inhibited MMP-7 activity at Ki=131.98±10.23 nM. Related MMPs such as MMP-14, -9 and -12 showed continued activity with negligible or no effect in the presence of GSM-192. E, The structure of the synthetic Zn Tripod mimicking highly conserved MMP active site is shown. In this structure Zn coordination with 3 histidines is conserved as in all MMP active sites. F, Dot blot showed selective binding of the anti MMP-7 Ab to activated form of the enzyme with high affinity at different concentrations. GSM-192 did not bind to the zymogen form.
Figure 2B:
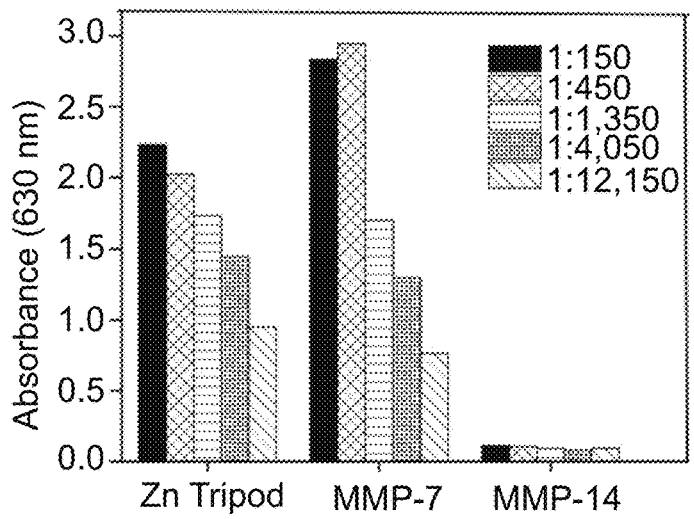

Alternating immunization strategy yields high affinity mAb selectively targeting MMP-7: GSM-192 was generated using alternate immunization of mice with the Zn Tripod and recombinant human MMP-7 (hMMP-7) active enzyme. Female BALB/c mice were immunized every 3 weeks with small Zn Tripod and the catalytic domain of hMMP-7 (see methods). The anti-Zn Tripod, anti-MMP-7 immune responses were examined in mouse serum using ELISA. Progressive responses were observed as a function of repetitive injection (FIG. 2A). Specificity of the immune responses in mouse serum was examined using ELISA against Zn Tripod (FIG. 2E) and the catalytic domain of MMP-7 respectively (FIG. 2B). This analysis indicated the generation of cross-reactive antibodies recognizing both Zn Tripod and MMP-7 (FIG. 2B).

Figure 2C:
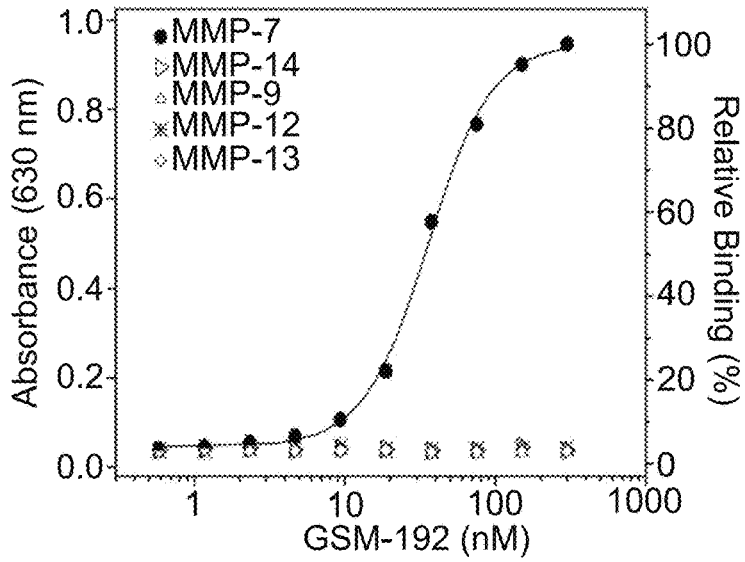
Figure 2D:
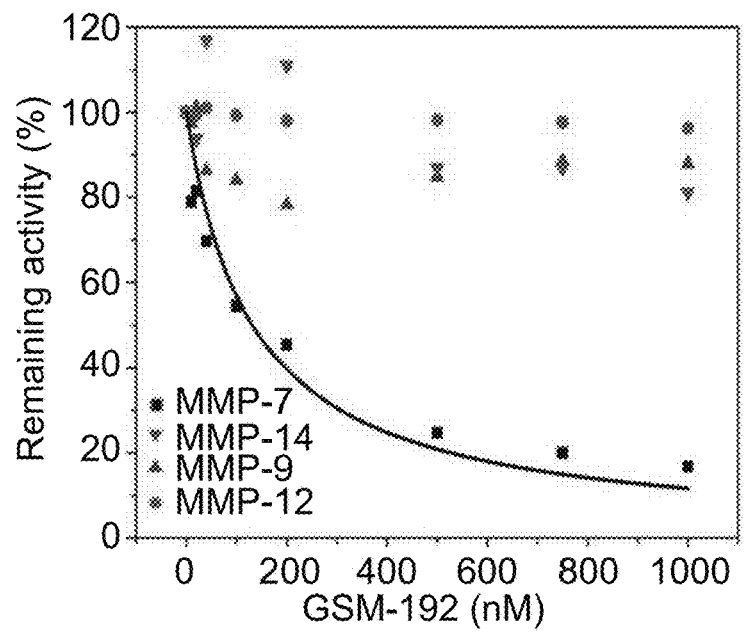
Figure 2E:
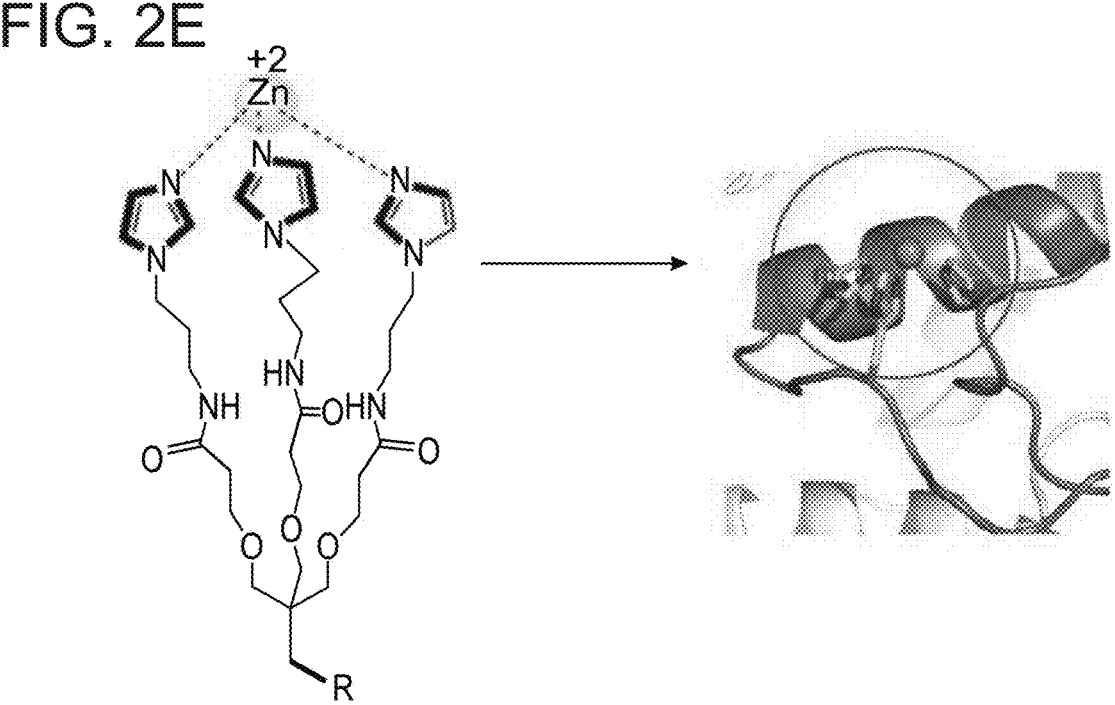
Figure 2F:
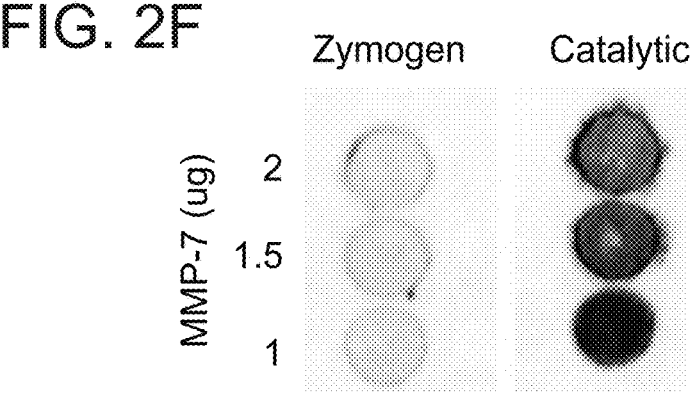

Only antibodies that were capable of binding to the activated form of MMP-7 and not the zymogen were selected for further development (i.e. selected for fusion and developed to generate monoclonal antibodies). This was carried out by dot blot analysis using a nitrocellulose membrane coated with varying concentrations of active MMP-7 and its zymogen respectively. It was shown that GSM-192 bound to the catalytic domain of the enzyme and not the zymogen form of the enzyme (FIG. 2F).

Selective binding of the MMP-7 catalytic domain and inhibition of catalytic activity: Binding constant of the selected anti MMP-7 mAb GSM-192 was measured using ELISA (FIG. 2C). The $K_d$ was measured to be 43.1±1.43 nM and the antibody did not show crossreactivity to closely related MMPs with conserved sequence homology and functional analogy such as MMP-9, -14, -12 and -13. The lack of binding to a panel of other MMPs helped measure the novel antibody's affinity to epitopes specifically unique to MMP-7.

Remarkably, considering that the immunization booster also included the common zinc motif, the antibody is fully selective for MMP-7. The effect of GSM-192 Fab fragment on the enzymatic activity of human MMP-7 was examined in vitro using a short fluorogenic peptide according to a standard protocol. The enzymatic activity of recombinant active MMP-7 was measured in the presence of increasing concentrations of the Fab fragment of GSM-192. GSM-192 Fab was found to inhibit MMP-7 activity with a $K_i$ of 131.98±10.23 nM. Simultaneously the effect of the antibody on catalytic activity of related MMPs was measured. The catalytic activities in vitro of MMP-9, -14 and -12 were either not affected or in the case of MMP-14 only negligibly affected by the anti MMP-7 Fab treatment (FIG. 2D).

Fab fragment crystal structure and docking model analysis with active MMP-7: To determine where the antibody was binding to inhibit the catalytic activity of MMP-7, GSM-192 Fab was characterized using X-ray crystallography. The crystal structure was determined at 2.3 Å resolution (FIG. 3A). The GSM-192 Fab construct is composed of 224 amino acid residues in the heavy chain and 215 amino acids in the light chain (439 residues in total). The final model includes residues 1-221 in the heavy chain and 2-185 in the light chain. The Rfree value is 27.85% (for the 5% of reflections not used in the refinement), and the Rwork value is 23.22% for all data to 2.3 Å (Table 1). The antigen binding surface is convoluted and exhibits two protruding elements, one consisting of light chain CDR1 (residues 31-DSYGN-35L) and the other of the heavy chain CDR3 (residues 101-GLRR-105H). This antigen-binding surface is unique and novel. The docking of GSM-192 (Fv domains) to MMP-7 produced a model (FIG. 3B) in which antibody loop CDR-H3 binds inside the active site of the enzyme.

The Protein Data Bank (PDB) includes several structures of the catalytic domain of MMP-7, which when overlaid show mobility of the loops near the active site. Similar mobility is seen in normal modes analysis and therefore antibody GSM-192 (Fv domains L2-L112 and Q0-Q116) was docked to several MMP-7 conformers that display different opening of the active site. Docking to MMP-7 conformer with an open active site, as seen in structure $2y6_{C31}$, produced the statistically outstanding model with complementarity score >3σ above the next model, shown in FIG. 3B.

The docking model implies that the binding is stabilized by strong hydrophobic anchoring of L100H in a pocket within MMP-7 active site, delimited by amino acids L181, A216 and Y241. Computational anchoring spots[32] mapping identified this pocket as a strong binder of hydrophobic residues, particularly Leu (FIG. 3B, D). Another strong hydrophobic interaction is the binding of Y33L in an elongated cavity on the surface of MMP-7 at the edge of the active site pocket. Additional predicted interactions are R105H-N243, T28HY172, Y32H-T180, N33H-P239/T240, N52H-H229, N55H-S101/G99, Y33L-P246/Q247, F37L-Y241, Y54L-G178 and E60L-N179.

Notably, the model shows that acetohydroxamic acid (AHA), a reversible zinc binding hydroxamate that binds directly in the catalytic cleft, can be accommodated in the binding site together with the antibody. FIG. 3C presents a view of predicted structure of the MMP-7/GSM-192 complex, highlighting the excellent surface complementarity on the one hand, and the small opening through which AHA can insert and bind to MMP-7 in the presence of GSM-192 on the other hand.

In summary, the proposed binding mode of the antibody consists of hydrophobic anchoring and numerous other contacts; it does not involve $Zn_{2+}$ and allows simultaneous binding of AHA to $Zn_{2+}$.

Lentiviral silencing reveals the important role of MMP-7 in pancreatic cancer cell survival in vitro: Western blot analysis was used to visualize the presence of MMP-7 in pancreatic cancer cell lines AsPC-1, Su86.86, BxPC-3, CFPAC-1. Cell lysates were blotted on membranes and probed with anti MMP-7 commercial antibody (monoclonal mouse IgG2B, R&D systems). The protein levels of active MMP-7, the zymogen and the intermediate form were found to vary in the cell lines (FIG. 6A). CFPAC-1 and ASPC-1 had high expression of all MMP-7 forms. The present inventors tested whether ablation of MMP-7 is, in principle, crucial for survival of the mono-cultured pancreatic cancer cells and carried out MMP-7 lentiviral silencing in AsPC-1 cells. The silencing resulted in cells that showed an augmented subG1 peak in propidium iodide (PI) staining and subsequent FACS analysis, indicating increased cell death compared to non-targeting control (FIG. 4A). Thus, pancreatic cancer cells were found to be sensitive to ablation of MMP-7.

Anti MMP-7 Fab induces pancreatic tumor cell death via apoptosis: To test the impact of antibody-mediated MMP-7 inhibition on pancreatic cancer cell death, 70% confluent cultures were treated with various GSM-192 Ab concentrations for 24 h. GSM-192-treatment led to induction of cell death. The cells were treated with MTT 3-(4,5-dimethylthiazol-2-yl)-2,5-diphenyltetrazolium bromide) to check the viability of cells and an $IC_{50}$ was calculated for standardized treatments in subsequent tests. CFPAC-1 and AsPC-1 PDAC cells died at an $IC_{50}$ of 4.34 µM and 2.33 µM respectively (FIG. 6B).

Anti LOXL-2 (Lysyl Oxidase like 2) $mAb_{33}$, produced in a similar pipeline was used as an isotype control. The GSM-192 Fab was shown to induce cell death via apoptosis and the proportion of the cell population undergoing apoptosis increased corresponding to the increasing concentrations of anti MMP-7 treatment (FIG. 4B). To test for molecular markers of apoptosis, Fas ligand expression was analysed by Western blot analysis. AsPC-1 cells were treated with GSM-192 Fab for 24 hours at sub lethal concentrations. Indeed, these cells showed an increase of Fas ligand (FasL) expression compared to untreated control (FIG. 4C).

GSM-192 Fab reduces cell motility in vitro: MMP-7 mediated E-Cadherin cleavage promotes cell migration[19], so it was hypothesized that an effective anti MMP-7 antibody directed to the activated enzyme should be able to impact migration. In a standard scratch assay (FIG. 5A) the GSM-192 treatment did not completely arrest cells from migrating but showed significant reduction in rate of wound closure (as controlled for anti-proliferative effect using Mitomycin C on CFPAC-1 cells in a prior experiment, data not shown). Indeed, GSM-192 treatment in sub-lethal concentrations reduced the number of cells able to migrate across the transwell membrane 15 h post treatment almost by half (FIG. 5B).

Evaluating the ability of native MMP7 in RIP1-Tag2 mice serum to bind anti MMP-7 antibody: Anti MMP-7 mAb was found to bind effectively to low concentrations of MMP-7 catalytic enzyme. Serum isolated from RIP1-Tag2 mice with late stage insulinomas were used to determine if anti MMP-7 mAb would be bound and removed by circulating enzyme. Very high concentrations of serum loaded on to the dot blot membrane did not show any binding of anti MMP-7 mAb (FIG. 8). The total serum protein loaded for this experiment was 335 times the protein concentration used for pure MMP-7 catalytic control. Selective binding of anti MMP-7 antibody to the catalytic form as demonstrated herein above may be the reason that no binding to circulating enzyme, mostly present in its zymogen form is observed.

GSM-192 treatment reduces occurrence of advanced tumor lesions in RIP1-Tag2 (PanNET) mice in early stage treatments: RIP1-Tag2 mice (n=15) in transition stage from hyperplastic to angiogenic stage spanning 6 to 8 weeks of age were treated with GSM-192 and GST control antibody at a concentration of 3 mg/kg every day intra peritoneal (IP). Animals at age 8 weeks post treatment was sacrificed and their pancreas was embedded in paraffin blocks and sectioned. Several sections in different depth in the tissue were made for subsequent histological analysis or immunofluorescence staining. Tumor sizes and staging was done in accordance with RIP1-Tag2 manual. The treatment was found to reduce progression of islets towards late angiogenesis, or in other words the fraction of islets advancing to post angiogenic lesions were reduced almost by half in the treated group (FIG. 9A). As previously observed in in-vitro cell culture, the tissue was tested for differences in cell proliferation rate (with cell division marker Ki-67) and in cell apoptosis rate (with effector apoptotic marker Caspase-3). No significant change in number of cells undergoing apoptosis or cell proliferation was observed (FIG. 9B). Significant changes in area covered by CD34+ cells were observed indicating that neo-angiogenic progenitor cells were less abundant in treated vs. control Ab group.

Late stage treatment shows sustained effect on tumor volume in RIP1-Tag2 (PanNET) mouse model: Late stage tumors in Rip1-Tag2 mice (n=15) from age 10 to 12 weeks post angiogenesis in their exponential growth stage was treated with GSM-192 and GST control antibody at a concentration of 5 mg/kg every other day in intra peritoneal (IP) injection. The total tumor burden calculated as tumor volume reduced significantly in GSM-192 treated group (FIG. 9C). The tumor volume was measured using x, y and z dimensions from a caliper scale. The tumor volume in the GSM-192 treated group reduced to less than half (from around 60 $mm^3$ to 24 $mm^3$) to of untreated group. The role of MMP-7 hence is important for tumor growth in late stages as well as in early stages, through overlapping or distinct mechanisms.

Tube formation by HUVEC cells were disrupted when treated with GSM-192: Human Umbilical Vein Endothelial Cells (HUVEC) was grown on Matrigel™ or similar ECM substrates for analysis of angiogenic tube formation. Formation of tubes or capillary like structures by HUVECs is a measure of promotion or reduction of angiogenesis potential. Following an 8 hour incubation with anti MMP-7 mAb GSM-192, both the number of branch points/nodes and the number of closed loops under a phase contrast inverted microscope were found to be significantly reduced compared to the control Ab treated HUVECs. The number of closed loops was reduced from a mean of 99 loops in GST control Ab treated group to a mean of 78 loops in GSM-192 wells (FIG. 10A). The number of branch points was also reduced from a mean of 107 to 83 nodes in treated group.

Aortic ring sprout assay showed marked reduction of neo vascular sprouts with GSM-192 treatment: The aortic ring assay is an ex-vivo assay to study angiogenesis potential without cell dissociation and provides a more complete picture of the complex events leading to micro-vessel formation. 8 week old mice aortas embedded in collagen type-1 were treated with GSM-192 and control GST mAb for 7 days. Fixed samples were stained with crystal violet and imaged under a microscope. The number of vascular sprouts was quantified. The average number of sprouts was significantly higher in control mAb treated samples than GSM-192 treated samples (FIG. 10B). It reduced from around 73 sprouts on average in GST treated samples to 43 sprouts in GSM-192 samples.

Co-treatment with GSM-192 decreases $IC_{50}$ of gemcitabine (GEM): Pancreatic ductal adenocarcinoma is inherently capable of robust resistance to chemotherapeutic agents. Dysregulation of Wnt/β-catenin pathway, which counts MMP-7 as a downstream target gene is implicated in acquiring of this drug resistance. MMP-7 via its shedding of Fas receptor has been shown to be involved in reducing sensitivity to the chemotherapeutic drug Oxaliplatin. The present inventors checked the effectiveness of GSM-192 in rescuing PDAC AsPC-1 cells from MMP-7 mediated drug resistance. Treatment of AsPC-1 cells yielded an $IC_{50}$ of 126.6±40.5 nM GEM+ PBS group. Co-treatment of 2.33 uM of GSM-192 and various concentrations of GSM-192 showed a marked reduction of $IC_{50}$ of GEM to 14.2±1.52 nM (FIGS. 11A-B). GSM-192, by inactivating MMP-7, increases the sensitivity of the cancer cells to GEM in vitro.

REFERENCES

1. White, R. J., Margolis, P. S., Trias, J. & Yuan, Z. Targeting metalloenzymes: a strategy that works. *Curr Opin Pharmacol* 3, 502-7 (2003).
2. Aharoni, A. et al. The 'evolvability' of promiscuous protein functions. *Nat Genet* 37, 73-6 (2005).
3. Bonnans, C., Chou, J. & Werb, Z. Remodelling the extracellular matrix in development and disease. *Nat Rev Mol Cell Biol* 15, 786-801 (2014).
4. Shiomi, T. & Okada, Y. MT1-MMP and MMP-7 in invasion and metastasis of human cancers. *Cancer Metastasis Rev* 22, 145-52 (2003).
5. Jackson, H. W., Defamie, V., Waterhouse, P. & Khokha, R. TIMPs: versatile extracellular regulators in cancer. *Nat Rev Cancer* 17, 38-53 (2017).
6. Murphy, G. Tissue inhibitors of metalloproteinases. *Genome Biol* 12, 233 (2011).
7. Jung, Y. S. et al. TIMP-1 induces an EMT-like phenotypic conversion in MDCK cells independent of its MMP-inhibitory domain. *PLoS One* 7, e38773 (2012).
8. Drews, J. Drug discovery: a historical perspective. *Science* 287, 1960-4 (2000).
9. Overall, C. M. & Kleifeld, O. Tumour microenvironment—opinion: validating matrix metalloproteinases as drug targets and anti-targets for cancer therapy. *Nat Rev Cancer* 6, 227-39 (2006).
10. Maurel, J. et al. Serum matrix metalloproteinase 7 levels identifies poor prognosis advanced colorectal cancer patients. *Int J Cancer* 121, 1066-71 (2007).
11. Wilson, C. L., Heppner, K. J., Labosky, P. A., Hogan, B. L. & Matrisian, L. M. Intestinal tumorigenesis is suppressed in mice lacking the metalloproteinase matrilysin. *Proc Natl Acad Sci USA* 94, 1402-7 (1997).
12. Rudolph-Owen, L. A., Chan, R., Muller, W. J. & Matrisian, L. M. The matrix metalloproteinase matrilysin influences early-stage mammary tumorigenesis. *Cancer Res* 58, 5500-6 (1998).
13. Crawford, H. C., Scoggins, C. R., Washington, M. K., Matrisian, L. M. & Leach, S. D. Matrix metalloproteinase-7 is expressed by pancreatic cancer precursors and regulates acinar-to-ductal metaplasia in exocrine pancreas. *J Clin Invest* 109, 1437-44 (2002).
14. Wagenaar-Miller, R. A. et al. Cooperative effects of matrix metalloproteinase and cyclooxygenase-2 inhibition on intestinal adenoma reduction. *Br J Cancer* 88, 1445-52 (2003).
15. Dufour, A. & Overall, C. M. Missing the target: matrix metalloproteinase antitargets in inflammation and cancer. *Trends Pharmacol Sci* 34, 233-42 (2013).
16. Strand, S. et al. Cleavage of CD95 by matrix metalloproteinase-7 induces apoptosis resistance in tumour cells. *Oncogene* 23, 3732-6 (2004).
17. Ito, T. K., Ishii, G., Chiba, H. & Ochiai, A. The VEGF angiogenic switch of fibroblasts is regulated by MMP-7 from cancer cells. *Oncogene* 26, 7194-203 (2007).
18. Patterson, B. C. & Sang, Q. A. Angiostatin-converting enzyme activities of human matrilysin (MMP-7) and gelatinase B/type IV collagenase (MMP-9). *J Biol Chem* 272, 28823-5 (1997).
19. McGuire, J. K., Li, Q. & Parks, W. C. Matrilysin (matrix metalloproteinase-7) mediates E-cadherin ectodomain shedding in injured lung epithelium. *Am J Pathol* 162, 1831-43 (2003).
20. McCawley, L. J. & Matrisian, L. M. Matrix metalloproteinases: they're not just for matrix anymore! *Curr Opin Cell Biol* 13, 534-40 (2001).
21. Lynch, C. C. et al. Matrix metalloproteinase 7 mediates mammary epithelial cell tumorigenesis through the ErbB4 receptor. *Cancer Res* 67, 6760-7 (2007).
22. Zhang, Q. et al. Interleukin-17 promotes prostate cancer via MMP7-induced epithelial-to-mesenchymal transition. *Oncogene* (2016).
23. Brabletz, T., Jung, A., Dag, S., Hlubek, F. & Kirchner, T. beta-catenin regulates the expression of the matrix metalloproteinase-7 in human colorectal cancer. *Am J Pathol* 155, 1033-8 (1999).
24. Wang, S. C. et al. A Pilot Study Evaluating Serum MMP7 as a Preoperative Prognostic Marker for Pancreatic Ductal Adenocarcinoma Patients. *J Gastrointest Surg* 20, 899-904 (2016).
25. Park, H. D. et al. Serum CA19-9, cathepsin D, and matrix metalloproteinase-7 as a diagnostic panel for pancreatic ductal adenocarcinoma. *Proteomics* 12, 3590-7 (2012).
26. Kuhlmann, K. F. et al. Evaluation of matrix metalloproteinase 7 in plasma and pancreatic juice as a biomarker for pancreatic cancer. *Cancer Epidemiol Biomarkers Prev* 16, 886-91 (2007).
27. Tamburrino, D. et al. Selection criteria in resectable pancreatic cancer: a biological and morphological approach. *World J Gastroenterol* 20, 11210-5 (2014).
28. Chari, S. T. et al. Early detection of sporadic pancreatic cancer: summative review. *Pancreas* 44, 693-712 (2015).
29. Sela-Passwell, N. et al. Antibodies targeting the catalytic zinc complex of activated matrix metalloproteinases show therapeutic potential. *Nat Med* 18, 143-7 (2011).
30. Knight, C. G., Willenbrock, F. & Murphy, G. A novel coumarin-labelled peptide for sensitive continuous assays of the matrix metalloproteinases. *FEBS Lett* 296, 263-6 (1992).
31. Otwinowski, Z. & Minor, W. Processing of X-ray diffraction data collected in oscillation mode. *Methods Enzymol* 276, 307-26 (1997).
32. Ben-Shimon, A. & Eisenstein, M. Computational mapping of anchoring spots on protein surfaces. *J Mol Biol* 402, 259-77 (2010).
33. Grossman, M. et al. Tumor Cell Invasion Can Be Blocked by Modulators of Collagen Fibril Alignment That Control Assembly of the Extracellular Matrix. *Cancer Res* 76, 4249-58 (2016).
34. Page-McCaw, A., Ewald, A. J. & Werb, Z. Matrix metalloproteinases and the regulation of tissue remodelling. *Nat Rev Mol Cell Biol* 8, 221-33 (2007).
35. Egeblad, M. & Werb, Z. New functions for the matrix metalloproteinases in cancer progression. *Nat Rev Cancer* 2, 161-74 (2002).

36. Fukuda, A. et al. Stat3 and MMP7 contribute to pancreatic ductal adenocarcinoma initiation and progression. *Cancer Cell* 19, 441-55 (2011).
37. Almendro, V. et al. The role of MMP7 and its cross-talk with the FAS/FASL system during the acquisition of chemoresistance to oxaliplatin. *PLoS One* 4, e4728 (2009).
38. Ametller, E. et al. Differential regulation of MMP7 in colon cancer cells resistant and sensitive to oxaliplatin-induced cell death. *Cancer Biol Ther* 11, 4-13 (2011).
39. Terwilliger, T. C. Maximum-likelihood density modification. *Acta Crystallogr D Biol Crystallogr* 56, 965-72 (2000).
40. French, S. & Wilson, K. On the treatment of negative intensity observations. *Acta Crystallographica Section A: Crystal Physics, Diffraction, Theoretical and General Crystallography* 34, 517-525 (1978).
41. McCoy, A. J. et al. Phaser crystallographic software. *J Appl Crystallogr* 40, 658-674 (2007).
42. Terwilliger, T. C. & Berendzen, J. Automated MAD and MIR structure solution. *Acta Crystallogr D Biol Crystallogr* 55, 849-61 (1999).
43. Emsley, P. & Cowtan, K. Coot: model-building tools for molecular graphics. *Acta Crystallogr D Biol Crystallogr* 60, 2126-32 (2004).
44. Laskowski, R. A., MacArthur, M. W., Moss, D. S. & Thornton, J. M. PROCHECK: a program to check the stereochemical quality of protein structures. *Journal of applied crystallography* 26, 283-291 (1993).
45. Suhre, K. & Sanejouand, Y. H. ElNemo: a normal mode web server for protein movement analysis and the generation of templates for molecular replacement. *Nucleic Acids Res* 32, W610-4 (2004).
46. Katchalski-Katzir, E. et al. Molecular surface recognition: determination of geometric fit between proteins and their ligands by correlation techniques. *Proc Natl Acad Sci USA* 89, 2195-9 (1992).
47. Heifetz, A., Katchalski-Katzir, E. & Eisenstein, M. Electrostatics in protein-protein docking. *Protein Sci* 11, 571-87 (2002).
48. Berchanski, A., Shapira, B. & Eisenstein, M. Hydrophobic complementarity in protein-protein docking. *Proteins* 56, 130-42 (2004).
49. Kowalsman, N. & Eisenstein, M. Combining interface core and whole interface descriptors in postscan processing of protein-protein docking models. *Proteins* 77, 297-318 (2009).
50. Kowalsman, N. & Eisenstein, M. Inherent limitations in protein-protein docking procedures. *Bioinformatics* 23, 421-6 (2007).
51. Pettersen, E. F. et al. UCSF Chimera—a visualization system for exploratory research and analysis. *J Comput Chem* 25, 1605-12 (2004).
52. Yee, J. K., Friedmann, T. & Burns, J. C. Generation of high-titer pseudotyped retroviral vectors with very broad host range. *Methods Cell Biol* 43 Pt A, 99-112 (1994).
53. Vermes, I., Haanen, C., Steffens-Nakken, H. & Reutelingsperger, C. A novel assay for apoptosis. Flow cytometric detection of phosphatidylserine expression on early apoptotic cells using fluorescein labelled Annexin V. *J Immunol Methods* 184, 39-51 (1995).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

In addition, any priority document(s) of this application is/are hereby incorporated herein by reference in its/their entirety.

---

What is claimed is:

1. A method of treating a disease associated with imbalanced or abnormal activity of MMP-7 in a subject in need thereof, the method comprising administering to the subject a therapeutically effective amount of an antibody, having complementarity determining region amino acid sequences as set forth in: SEQ ID NOs: 3, 4 and 5, sequentially arranged from N to C on a light chain of the antibody; and SEQ ID NOs: 6, 7 and 8, sequentially arranged from N to C on a heavy chain of the antibody, thereby treating the disease associate with imbalanced or abnormal activity of MMP-7 in the subject.

2. The method of claim 1, wherein the disease is cancer.

3. The method of claim 2, wherein the cancer is pancreatic cancer.

4. The method of claim 3, wherein the pancreatic cancer is pancreatic adenocarcinoma.

5. A method of treating cancer in a subject in need thereof comprising:
   (a) analyzing in a sample of the subject for an amount of MMP-7; and
   (b) administering to the subject a therapeutically effective amount of an antibody which having complementarity determining region amino acid sequences as set forth in: SEQ ID NOs: 3, 4 and 5, sequentially arranged from N to C on a light chain of the antibody; and SEQ ID NOs: 6, 7 and 8, sequentially arranged from N to C on a heavy chain of the antibody upon confirmation that said amount of said MMP-7 is above a predetermined level, thereby treating the cancer.

6. The method of claim 5, wherein said analyzing is effected using an antibody.

7. A method of treating cancer in a subject in need thereof comprising:
   (a) analyzing in a sample of the subject for an amount of MMP-7 using an antibody having complementarity determining region amino acid sequences as set forth in: SEQ ID NOs: 3, 4 and 5, sequentially arranged from N to C on a light chain of the antibody; and SEQ ID NOs: 6, 7 and 8, sequentially arranged from N to C on a heavy chain of the antibody; and
   (b) administering to the subject a therapeutically effective amount of an agent which down-regulates the amount of said MMP-7 upon confirmation that said amount of said MMP-7 is above a predetermined level, thereby treating the cancer.

8. A method of treating pancreatic cancer in a subject in need thereof comprising administering to the subject a therapeutically effective amount of an antibody which down-regulates MMP-7 activity and a chemotherapeutic agent, wherein the antibody inhibits the activity of said MMP-7 and wherein the Ki of the antibody towards said MMP-7 is at least 5 times lower than a Ki of the antibody towards MMP2 or MMP9, thereby treating the pancreatic cancer, wherein the antibody has complementarity determining region amino acid sequences as set forth in: SEQ ID NOs: 3, 4 and 5, sequentially arranged from N to C on a light chain of the antibody;
   and SEQ ID NOs: 6, 7 and 8, sequentially arranged from N to C on a heavy chain of the antibody.

9. The method of claim 8, wherein said chemotherapeutic agent is a nucleoside analogue.

10. The method of claim 9, wherein said nucleoside analogue comprises gemcitabine.

11. The method of claim 8, wherein said chemotherapeutic agent is Oxaliplatin.

12. The method of claim 8, wherein the dose of said chemotherapeutic agent is less than the gold standard dose when used as a single agent.

13. An article of manufacture comprising an antibody, having complementarity determining region CDR amino acid sequences as set forth in: SEQ ID NOs: 3, 4 and 5, sequentially arranged from N to C on a light chain of the antibody; and SEQ ID NOs: 6, 7 and 8, sequentially arranged from N to C on a heavy chain of the antibody and a chemotherapeutic agent.

14. The article of manufacture of claim 13, wherein said chemotherapeutic agent is a nucleoside analogue.

15. The article of manufacture of claim 14, wherein said nucleoside analogue comprises gemcitabine.

16. The article of manufacture of claim 13, wherein said chemotherapeutic agent is Oxaliplatin.

17. The article of manufacture of claim 13, wherein said antibody and said chemotherapeutic agent are formulated in a single composition.

* * * * *

SEQUENCE LISTING

```
<160> NUMBER OF SEQ ID NOS: 10

<210> SEQ ID NO 1
<211> LENGTH: 112
<212> TYPE: PRT
<213> ORGANISM: Artificial sequence
<220> FEATURE:
<223> OTHER INFORMATION: GSM-192 Light Chain Sequence

<400> SEQUENCE: 1

Asp Ile Val Thr Gln Ser Pro Ala Ser Leu Ala Val Ser Leu Gly Gln
1               5                   10                  15

Arg Ala Thr Ile Ser Cys Arg Ala Ser Glu Ser Phe Asp Ser Tyr Gly
            20                  25                  30

Asn Thr Phe Val His Trp Tyr Gln Gln Lys Pro Gly Gln Pro Pro Lys
        35                  40                  45

Leu Leu Ile Tyr Leu Val Ser Asn Leu Glu Ser Gly Val Pro Ala Gly
    50                  55                  60

Phe Arg Gly Arg Gly Ser Arg Thr Asp Phe Thr Leu Thr Ile Asp Pro
65                  70                  75                  80
```

Val Glu Ala Asp Asp Ala Ala Thr Tyr Tyr Cys Gln Gln Asn Asn Glu
                85                  90                  95

Asp Pro Tyr Thr Phe Gly Gly Thr Lys Leu Glu Ile Lys Arg Ala
            100                 105                 110

<210> SEQ ID NO 2
<211> LENGTH: 119
<212> TYPE: PRT
<213> ORGANISM: Artificial sequence
<220> FEATURE:
<223> OTHER INFORMATION: GSM-192 Heavy Chain Sequence

<400> SEQUENCE: 2

Glu Val Gln Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
            20                  25                  30

Asn Met Asp Trp Met Lys Gln Ser His Gly Lys Ser Leu Glu Trp Ile
        35                  40                  45

Gly His Ile Asn Pro Asn Asn Gly Gly Thr Phe Tyr Asn Gln Lys Phe
    50                  55                  60

Lys Asp Lys Ala Thr Phe Ile Val Asp Lys Ser Ser Thr Ala Tyr
65                  70                  75                  80

Met Glu Leu Arg Ser Leu Thr Ser Glu Asp Thr Ala Val Tyr Phe Cys
                85                  90                  95

Ala Arg Gly Gly Gly Leu Arg Arg Gly Pro Phe Ala Tyr Trp Gly Gln
            100                 105                 110

Gly Thr Leu Val Thr Val Ser
        115

<210> SEQ ID NO 3
<211> LENGTH: 14
<212> TYPE: PRT
<213> ORGANISM: Artificial sequence
<220> FEATURE:
<223> OTHER INFORMATION: complementarity determining region (CDR) amino
      acid sequences

<400> SEQUENCE: 3

Ala Ser Glu Ser Phe Asp Ser Tyr Gly Asn Thr Phe Val His
1               5                   10

<210> SEQ ID NO 4
<211> LENGTH: 6
<212> TYPE: PRT
<213> ORGANISM: Artificial sequence
<220> FEATURE:
<223> OTHER INFORMATION: complementarity determining region (CDR) amino
      acid sequences

<400> SEQUENCE: 4

Leu Val Ser Asn Leu Glu
1               5

<210> SEQ ID NO 5
<211> LENGTH: 8
<212> TYPE: PRT
<213> ORGANISM: Artificial sequence
<220> FEATURE:
<223> OTHER INFORMATION: complementarity determining region (CDR) amino
      acid sequences

<400> SEQUENCE: 5

Gln Gln Asn Asn Glu Asp Pro Tyr
1               5

<210> SEQ ID NO 6
<211> LENGTH: 8
<212> TYPE: PRT
<213> ORGANISM: Artificial sequence
<220> FEATURE:
<223> OTHER INFORMATION: complementarity determining region (CDR) amino
      acid sequences

<400> SEQUENCE: 6

Gly Tyr Thr Phe Thr Asp Tyr Asn
1               5

<210> SEQ ID NO 7
<211> LENGTH: 10
<212> TYPE: PRT
<213> ORGANISM: Artificial sequence
<220> FEATURE:
<223> OTHER INFORMATION: complementarity determining region (CDR) amino
      acid sequences

<400> SEQUENCE: 7

His Ile Asn Pro Asn Asn Gly Gly Thr Phe
1               5                   10

<210> SEQ ID NO 8
<211> LENGTH: 8
<212> TYPE: PRT
<213> ORGANISM: Artificial sequence
<220> FEATURE:
<223> OTHER INFORMATION: complementarity determining region (CDR) amino
      acid sequences

<400> SEQUENCE: 8

Gly Gly Gly Leu Arg Arg Gly Pro
1               5

<210> SEQ ID NO 9
<211> LENGTH: 15
<212> TYPE: PRT
<213> ORGANISM: Artificial sequence
<220> FEATURE:
<223> OTHER INFORMATION: Biotin ligase tag amino acid sequence

<400> SEQUENCE: 9

Leu His His Ile Leu Asp Ala Gln Lys Met Val Trp Asn His Arg
1               5                   10                  15

<210> SEQ ID NO 10
<211> LENGTH: 7
<212> TYPE: PRT
<213> ORGANISM: Artificial sequence
<220> FEATURE:
<223> OTHER INFORMATION: fluorogenic peptide
<220> FEATURE:
<221> NAME/KEY: MISC_FEATURE
<222> LOCATION: (1)..(1)
<223> OTHER INFORMATION: Mca [(7-Methoxycoumarin-4-yl)acetyl] conjugated
<220> FEATURE:
<221> NAME/KEY: MISC_FEATURE

```
<222> LOCATION: (5)..(5)
<223> OTHER INFORMATION: X= Dpa: N-3-(2,4-Dinitrophenyl)-L-2,3-
      diaminopropionyl

<400> SEQUENCE: 10

Pro Leu Gly Leu Xaa Ala Arg
1               5
```